(12) United States Patent
Takemoto et al.

(10) Patent No.: US 7,575,548 B2
(45) Date of Patent: Aug. 18, 2009

(54) ENDOSCOPIC TREATMENT INSTRUMENT, ENDOSCOPIC TREATMENT SYSTEM AND SUPPORTING ADAPTOR

(75) Inventors: Shotaro Takemoto, Tokyo (JP); Tetsuya Yamamoto, Hanno (JP); Yoshio Onuki, Hino (JP); Koichi Kawashima, Hachioji (JP); Yuji Sakamoto, Hachioji (JP)

(73) Assignee: Olympus Corporation, Tokyo (JP)

( * ) Notice: Subject to any disclaimer, the term of this patent is extended or adjusted under 35 U.S.C. 154(b) by 712 days.

(21) Appl. No.: 11/208,388

(22) Filed: Aug. 19, 2005

(65) Prior Publication Data

US 2006/0069304 A1 Mar. 30, 2006

(30) Foreign Application Priority Data

Sep. 24, 2004 (JP) ............................. 2004-277028

(51) Int. Cl.
*A61B 1/00* (2006.01)
(52) U.S. Cl. ..................... 600/104; 600/106; 600/121; 600/122; 600/123; 600/127; 600/129; 600/153
(58) Field of Classification Search ................. 600/104, 600/106, 121, 127, 129
See application file for complete search history.

(56) References Cited

U.S. PATENT DOCUMENTS

| | | | |
|---|---|---|---|
| 5,984,932 A * | 11/1999 | Yoon ........................... 606/147 |
| 6,022,313 A * | 2/2000 | Ginn et al. ................... 600/114 |
| 6,071,233 A | 6/2000 | Ishikawa et al. |
| 6,352,503 B1 | 3/2002 | Matsui et al. |
| 6,786,864 B2 * | 9/2004 | Matsuura et al. ............ 600/104 |
| 6,878,106 B1 * | 4/2005 | Herrmann .................... 600/104 |
| 6,988,985 B2 * | 1/2006 | Suzuki et al. ................ 600/104 |
| 7,306,613 B2 * | 12/2007 | Kawashima et al. ......... 606/148 |
| 7,416,554 B2 * | 8/2008 | Lam et al. .................... 606/153 |
| 7,431,694 B2 * | 10/2008 | Stefanchik et al. .......... 600/104 |
| 2003/0181924 A1 | 9/2003 | Yamamoto et al. |
| 2003/0195387 A1 | 10/2003 | Kortenbach et al. |

FOREIGN PATENT DOCUMENTS

WO WO 95/18562 7/1995

* cited by examiner

*Primary Examiner*—Linda C Dvorak
*Assistant Examiner*—Matthew J Kasztejna
(74) *Attorney, Agent, or Firm*—Scully, Scott, Murphy & Presser, P.C.

(57) ABSTRACT

In an endoscopic treatment instrument having a plurality of sheaths, a supporting member for directly and indirectly supporting the plurality of sheaths, and a connecting member for directly/indirectly bringing the sheaths and an endoscope in a connected state are provided. The supporting member constrains a relative position of the plurality of sheaths and the connecting member can change the connecting state. Therefore, when an operator changes the connecting state of the connecting member, the positional relation of the endoscope and the plurality of sheaths can be changed, while the positional relation of the plurality of sheaths is still constrained. Accordingly, for example, left and right sheaths can be easily exchanged.

11 Claims, 24 Drawing Sheets

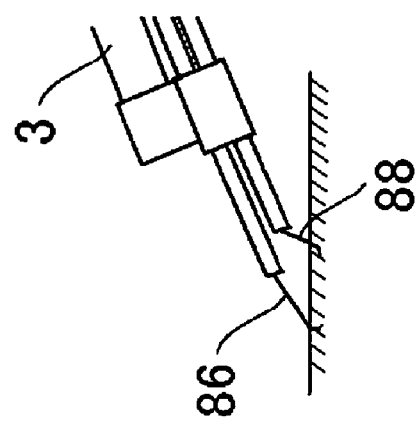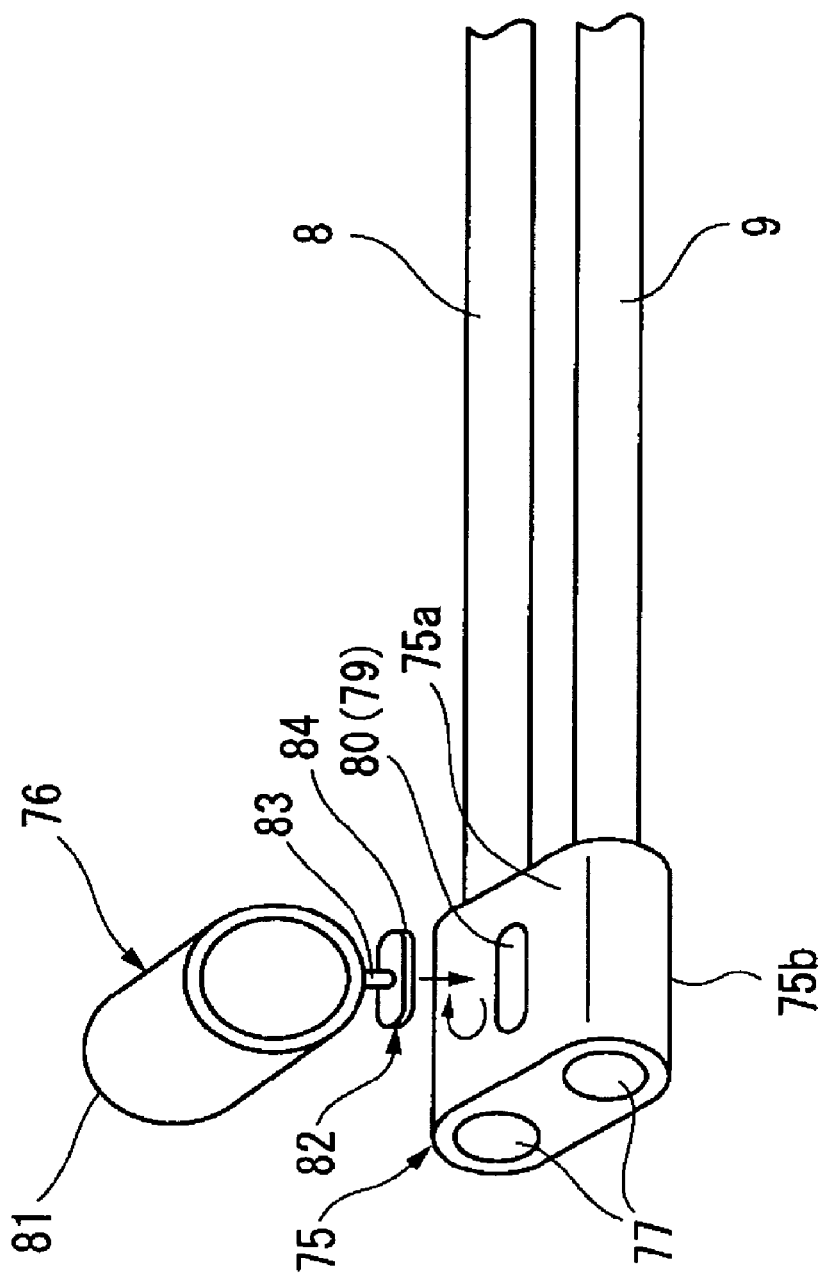
Fig. 13A
Fig. 13B

ENDOSCOPIC TREATMENT INSTRUMENT, ENDOSCOPIC TREATMENT SYSTEM AND SUPPORTING ADAPTOR

CROSS-REFERENCE TO RELATED APPLICATION

This application is based upon and claims the benefit of priority from prior Japanese Patent Application No. 2004-277028, filed Sep. 24, 2004, the entire contents of which is incorporated herein by reference.

BACKGROUND OF THE INVENTION

1. Field of the Invention

The present invention relates to an endoscopic treatment instrument and a supporting adaptor to be used with an endoscope, and an endoscopic treatment system including the endoscope.

2. Description of the Related Art

An endoscopic treatment instrument (hereinafter, referred to as an instrument) is inserted into a body with an endoscope for carrying out a treatment for living organisms, and includes a distal treatment unit provided at a distal end of an elongated flexible sheath.

As the diameter of a forceps channel formed in the endoscope is small, the diameter of the instrument which can be inserted into the forceps channel is limited. Therefore, when a large sized instrument is to be used, an external channel can be provided outside an endoscope insertion part, and the sheath of the instrument is inserted through the external channel. The external channel extends substantially along the entire length of the endoscope insertion part. There is an endoscope of a type in which the external channel is fixed to the insertion part in such a manner that a wire is extended from a distal end portion of the external channel, a loop formed at a distal end of the wire is hooked to a distal end of the insertion part, and the external channel and the endoscope are engaged by a frictional force (for example, see JP-A-2002-143078).

There is also a type in which two of such external channels are mounted to the endoscope insertion part in parallel with each other, the sheath of the instrument is inserted into the external channels, and a needle of a suture instrument and a needle receiving unit are provided as a distal end treatment unit at a distal end of each sheath (for example, see the specification of U.S. patent application Publication No. 2003/0181924).

However, when a plurality of instruments are disposed along an outer surface of the endoscope insertion part for carrying out a treatment, in some cases, it may be effective to exchange the distal end treatment units between a left side and a right side (or between a upper side and a lower side) depending on conditions of an affected area and the direction of approach of the endoscope. In such cases, when the entire endoscope is rotated in order to exchange the distal end treatment units between the left side and the right side, the field of view of the endoscope is also rotated correspondingly, and hence it makes operation difficult for an operator.

In view of such circumstances, it is an object of the invention to enable treatment units at distal ends to be exchanged between left and right sides (or upper and lower sides) without rotating an endoscope.

BRIEF SUMMARY OF THE INVENTION

An endoscopic treatment instrument of the invention is inserted into a body with an endoscope insertion part for carrying out a treatment for living organisms and includes a plurality of elongated flexible sheaths, an operating part provided at a proximal portion of each of the elongated flexible sheaths, and a distal end treatment unit provided at a distal portion of each of the plurality of elongated flexible sheaths for carrying out a treatment for living organisms. In addition, the endoscopic treatment instrument includes a supporting member for directly or indirectly supporting the plurality of elongated flexible sheaths disposed substantially in parallel with the endoscope insertion part for constraining a relative position between the plurality of elongated flexible sheaths, and a connecting member for directly or indirectly connecting the plurality of elongated flexible sheaths and the endoscope insertion part.

It is configured in such a manner that an operator can change the arrangement of the plurality of sheaths with respect to the endoscope insertion part by changing a connecting state of the connecting member.

The endoscopic treatment instrument is mounted to the endoscope insertion part via the connecting member in a state in which the arrangement of the plurality of elongated flexible sheaths, along with the arrangement of the distal end of treatment units inserted therein, is fixed by the supporting member. In this case, when a change of the arrangement of the distal end treatment units is desired, the operator changes the connecting state of the connecting member. Then, the positional relation between the distal end treatment units and the endoscope can be changed while the relative arrangement of the distal end treatment units is preserved.

When the connecting state of the connecting member is changed, for example, a state in which the supporting member is rotated at least about a longitudinal axis which extends substantially in parallel with a longitudinal axis of the endoscope insertion part is achieved. This rotated state includes a state in which the supporting member is turned to an upside down position about the longitudinal axis which extends substantially in parallel with the longitudinal axis of the endoscope insertion part.

The connecting member may be provided with a rotary supporting section that supports one of the plurality of elongated flexible sheaths so as to be capable of rotating about the longitudinal axis.

In this endoscopic treatment instrument, when change of the arrangement of the plurality of elongated flexible sheaths is desired, the operator rotates the supporting member about the longitudinal axis of one of the plurality of elongated flexible sheaths which is supported by the rotary supporting section with respect to the rotary supporting section.

The connecting member may be provided with an engaging section that engages with the insertion part so as to be capable of rotating about the longitudinal axis of the endoscope insertion part.

In this endoscopic treatment instrument, the connecting member can be mounted at different angles with respect to a longitudinal axis of the endoscope insertion part. Therefore, when the connecting member is mounted at a position rotated by 180 degrees with respect to the endoscope insertion part, the arrangement of the plurality of elongated flexible sheaths can be inverted in appearance.

Furthermore, the engaging section can be detachably attached to the endoscope insertion part. In this arrangement, the arrangement of the plurality of elongated flexible sheaths can be changed in a state in which the connecting member is removed from the endoscope insertion part.

The connecting member may be provided with a plurality of plurality of elongated flexible sheaths supporting sections for supporting the plurality of elongated flexible sheaths so as to be capable of replacing each other.

In this arrangement, when the plurality of elongated flexible sheaths are allocated to the sheath supporting sections of the connecting member one by one, the arrangement of the plurality of elongated flexible sheaths is fixed. From this state, when the combination of the sheath supporting sections and the plurality of elongated flexible sheaths is changed, the arrangement of the plurality of elongated flexible sheaths can be changed.

In addition, the supporting member may be provided with mounting parts for fixing the supporting member to the endoscope insertion part. The number of the mounting parts can be the same number of the possible arrangements of the plurality of elongated flexible sheaths.

This endoscopic treatment instrument is provided with a plurality of the mounting parts so that the arrangement of the plurality of elongated flexible sheaths can be changed. For example, when there are two sheaths provided therein, there are two possible arrangements and thus two of the mounting parts are provided. When three of the sheaths are arranged in a triangular shape, there are three possible arrangements, and thus three of the mounting parts are provided.

The connecting member may be provided so as to be capable of moving substantially in the orthogonal direction with respect to a plane that is defined by the plurality of elongated flexible sheaths.

In this endoscopic treatment instrument, when the connecting member is moved to project in the direction perpendicular to the plane defined by the plurality of elongated flexible sheaths, the plurality of elongated flexible sheaths are mounted on the endoscope according to the connecting member's direction directing the endoscope insertion part. In contrast, when the connecting member is caused to project in another direction, the plurality of elongated flexible sheaths can be mounted to the endoscope in the opposite arrangement from the case described above.

This invention can be considered as an invention of an endoscopic system including the above endoscope treatment instrument and the endoscope. The endoscope may be provided with a fixing part with which the connecting member engages (for example, a groove formed one or more side surfaces of the endoscope).

The invention may also be considered to be a supporting adaptor for the endoscopic treatment instrument.

According to the invention, the endoscopic treatment instrument can be externally attached to the endoscope easily via the connecting member. Also, change of the arrangement of the plurality of elongated flexible sheaths with respect to the endoscope can be achieved, for example, by rotating the treatment instrument system while fixing the relative positional relation of the plurality of distal end treatment units by the supporting member. Therefore, the arrangement of the distal end treatment units on a display of the endoscope can be changed, for example, without re-inserting the treatment units into the sheaths. Therefore, the manipulation thereof is facilitated, and hence the time required for manipulation can be reduced.

BRIEF DESCRIPTION OF THE SEVERAL VIEWS OF THE DRAWINGS

These and other features, aspects, and advantages of the apparatus and methods of the present invention will become better understood with regard to the following description, appended claims, and accompanying drawings where:

FIG. 13A is an explanatory drawing of a principle of a mechanism for attaching and detaching the supporting member and the connecting member;

FIG. 13B is an explanatory drawing showing a state in which the living organism is pinched:

DETAILED DESCRIPTION OF THE PREFERRED EMBODIMENTS

Preferred embodiments are described below with reference to the accompanying drawings.

Figure 1:
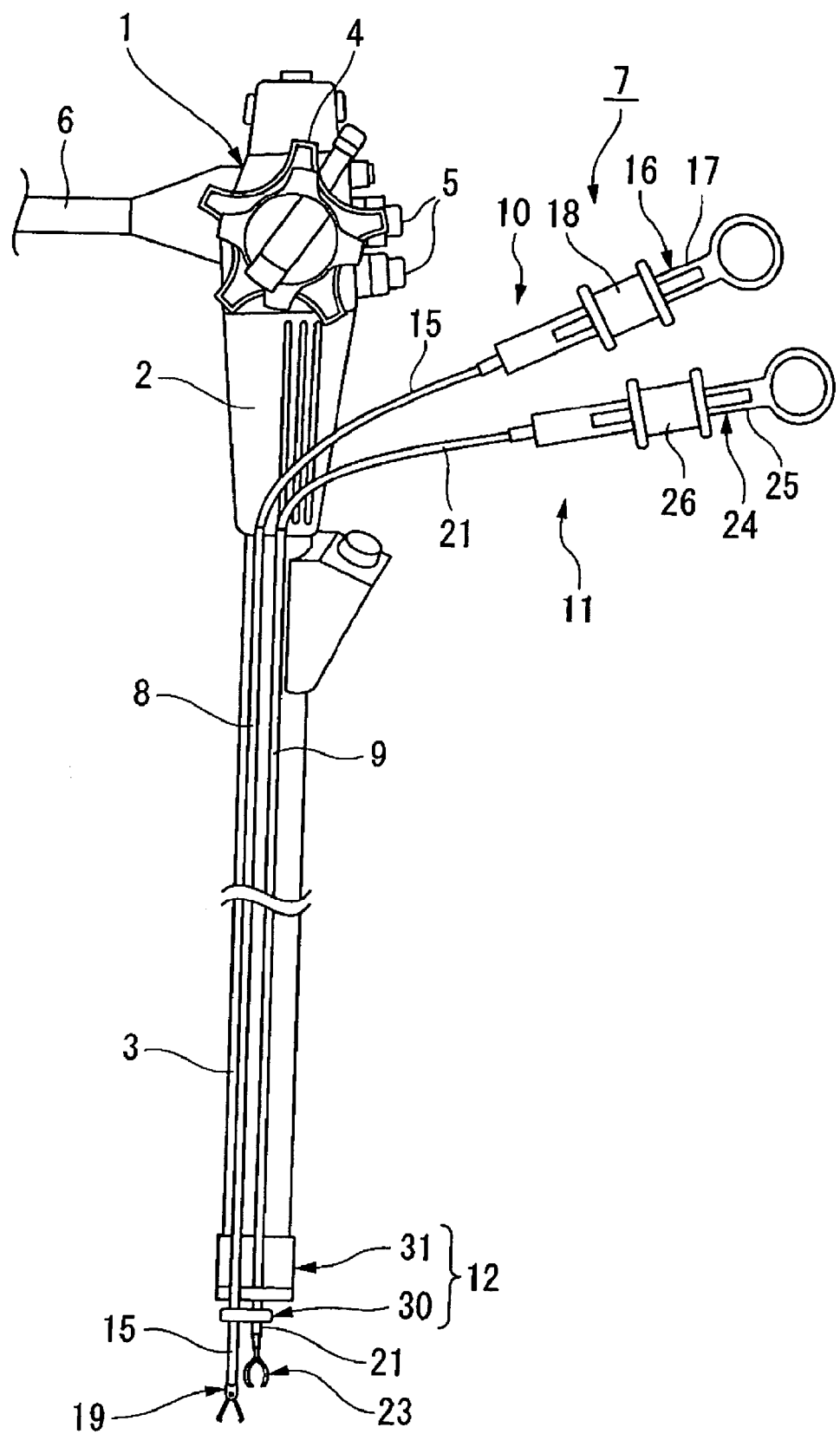
FIG. 1 is a schematic diagram of an endoscopic treatment system according to a first embodiment.

FIG. 1 shows a state in which an endoscopic treatment instrument according to a first embodiment is mounted to an endoscope.

The endoscope 1 is provided with an endoscope insertion part (hereinafter, referred to as insertion part) 3 at a distal end of an operating part 2 which is operated by an operator. The insertion part 3 has an elongated shape and has flexibility, and is provided with a CCD, an illumination means, and the like at a distal portion thereof. The operating part 2 includes a knob 4 for bending the distal portion of the insertion part 3, switches 5, a universal cord 6, and so on. The endoscope 1 in this configuration is externally attached with endoscopic treatment instruments (hereinafter referred to as the treatment instruments) 7 in a state of being inserted into two of first and second external channels 8, 9 as tubular members. The first external channel 8 and the second external channel 9 are flexible sheaths. The first external channel 8 and the second external channel 9 each are formed with a lumen which penetrates therein along the length thereof, and are detachably mounted substantially parallel with the insertion part 3.

The treatment instruments 7 include a pinching forceps 10 and a clip 11 to be inserted respectively through the first and second external channels 8, 9 to be externally attached to the insertion part 3, and a supporting adaptor 12 for supporting and positioning the pinching forceps 10 and the clip 11 in a predetermined arrangement.

The pinching forceps 10 include a flexible sheath 15 that is to be inserted into the first external channel 8 so as to be capable of moving back and forth (distally and proximally). A proximal portion of the sheath 15 extends beyond a proximal end of the first external channel 8, and an operating part 16 is attached thereto. The operating part 16 includes an operating part body 17 and a slider 18 which can slide with respect thereto. A distal portion of the sheath 15 projects from a distal end of the first external channel 8, where a distal end treatment unit 19 is mounted thereto. The distal end treatment unit 19 includes a pair of pinching members 20 which can be opened and closed (see FIG. 2). The pinching members 20 include an operating wire (not shown) connected thereto, and the operating wire is inserted into the sheath 15 so as to be capable of moving back and forth, and is fixed to the slider 18 of the operating part 16. Therefore, when the operator moves the slider 18 forward, the pair of pinching members 20 are opened, and when the operator moves the slider 18 backward, the pair of pinching members 20 are closed.

The clip 11 includes a flexible sheath 21 that is inserted into the second external channel 9 so as to be capable of moving back and forth, and a flexible pusher 22 (see FIG. 2) inserted into the sheath 21 so as to be capable of moving back and forth. A clip unit 23, which is a distal end treatment unit, for clipping an anatomy is attached to a distal end of the pusher 22. A proximal portion of the sheath 21 extends beyond a proximal end of the second external channel 9, and an operating part 24 is attached thereto. A slider 26 is mounted to a main body 25 of the operating part 24 so as to be capable of moving back and forth, and a proximal portion of the pusher 22 is fixed to the slider 26.

Figure 2:
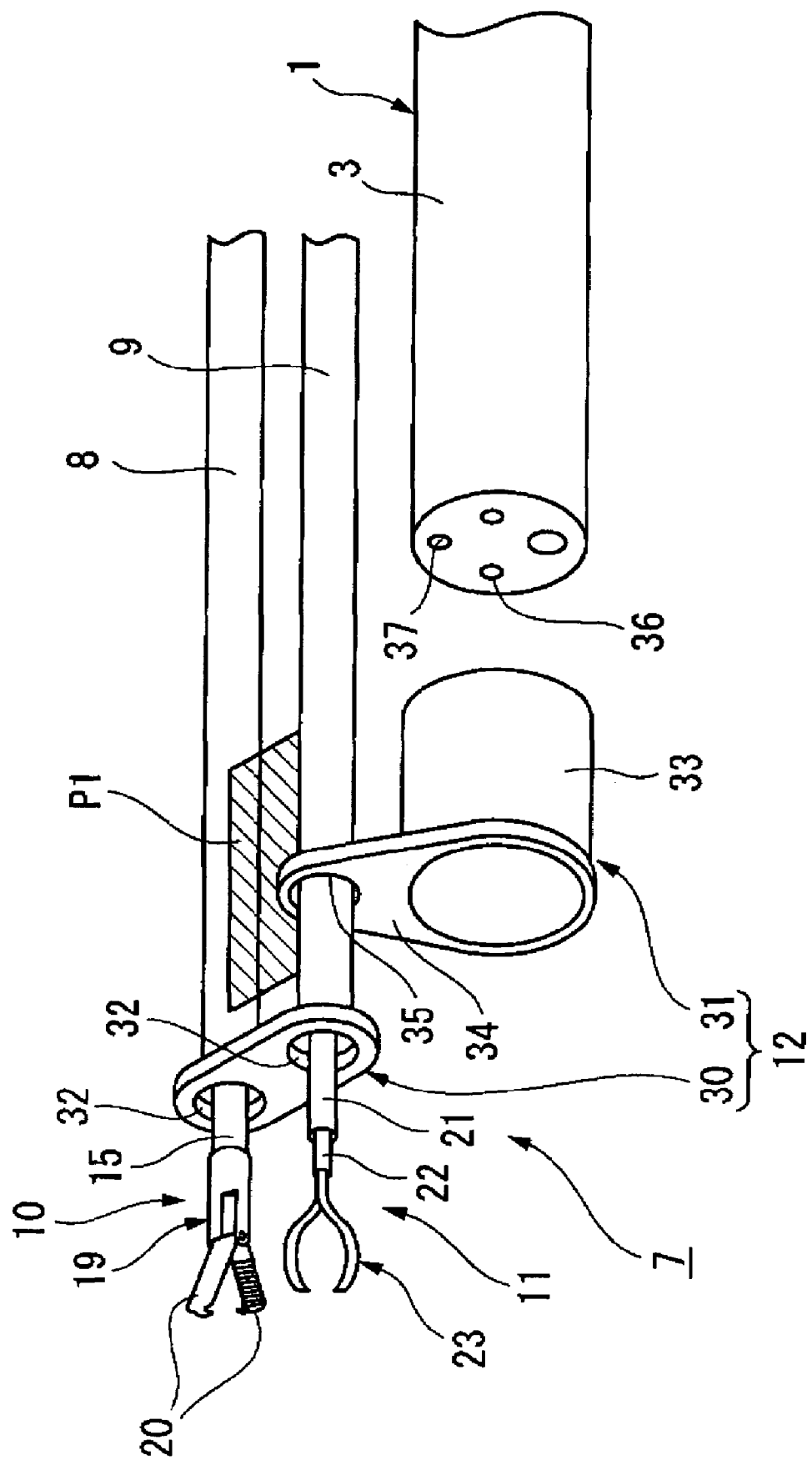
FIG. 2 is a perspective view showing a configuration of a distal portion of the treatment instrument of FIG. 1.

As shown in FIG. 2, the supporting adapter 12 includes a supporting member 30 as a supporting portion to which the distal portions of the two external channels 8, 9 are fixed, and a fixing cap (connecting member) 31 as a connecting portion. The supporting member 30 is formed with two through holes 32 on an elongated plate so as to extend in parallel with each other at a predetermined distance from each other, and the two external channels 8, 9 are fixed to these through holes 32 with their respective lumen communicated to the environment through these through holes 32. The fixing cap 31 includes a cylindrical engaging section 33 through which the insertion part 3 of the endoscope 1 can be inserted, and a distal portion of the engaging section 33 extends radially outwardly to form a sheath supporting section 34. The sheath supporting section 34 is formed with a through hole 35, which corresponds to a rotary supporting section through which the second external channel 9 is rotatably supported.

Subsequently, the operation of the first embodiment will be described.

Figure 3:
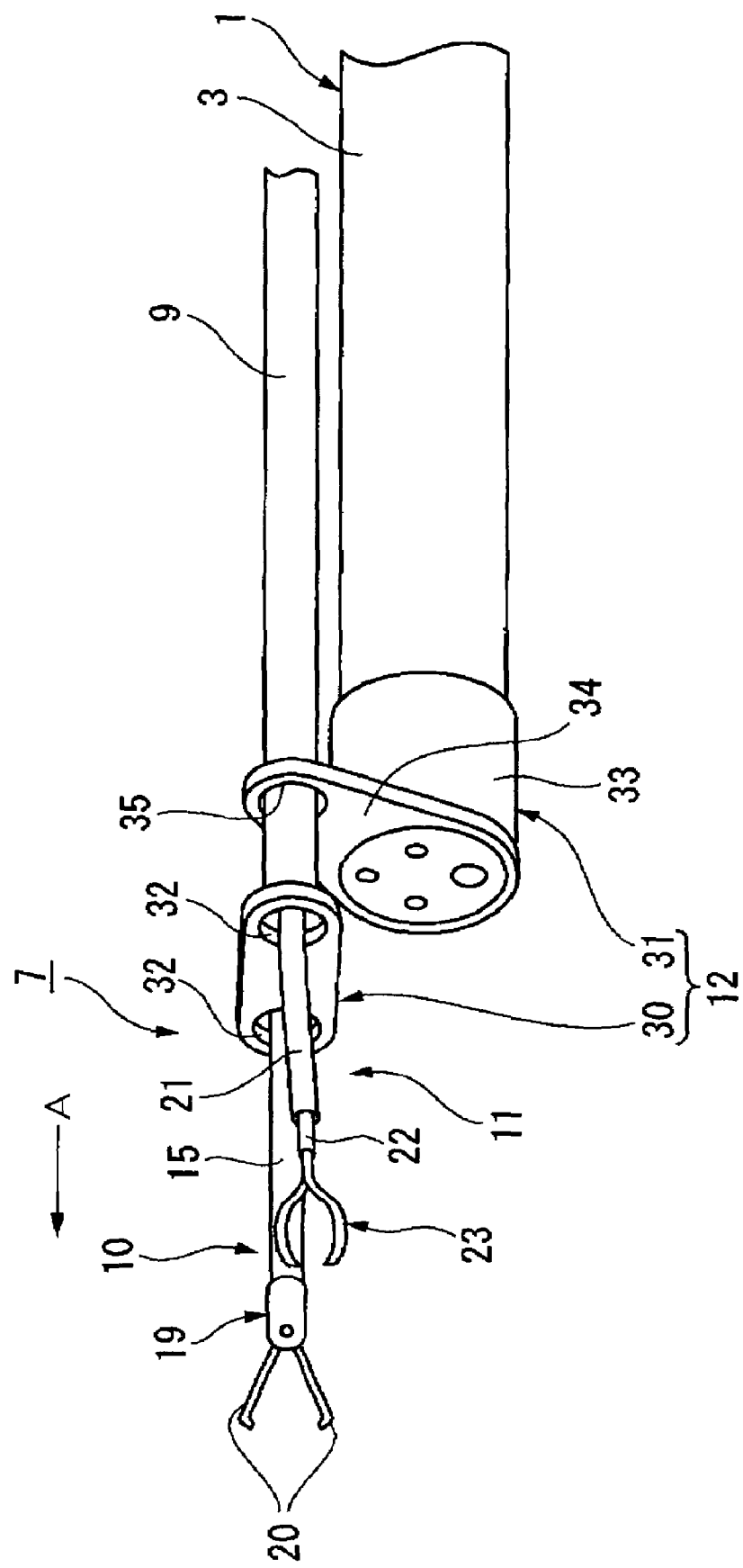
FIG. 3 is a drawing showing a state in which the treatment instrument of FIG. 2 is attached to an endoscope.

As shown in FIGS. 1-3, the operator arranges the respective external channels 8, 9 substantially parallel to each other along the insertion part 3, and fits the fixing cap 31 at the distal portion of the inserting portion 3. Subsequently, the operator inserts the pinching forceps 10 from the proximal side of the first external channel 8 and inserts the clip 11 from the proximal side of the second external channel 9. In this case, as shown in FIG. 3, the pinching forceps 10 is arranged on the right side and the clip 11 is arranged on the left side when viewed from the insertion part 3 toward an object to be treated in a direction indicated by Arrow A. Although the positions of the pinching forceps 10 and the clip 11 are fixed by friction between the external channels 8, 9 and the insertion part 3, the external channels 8, 9 may be fixed to the insertion part 3 by other means, such as with tape when the friction force is not strong enough.

Figure 4:
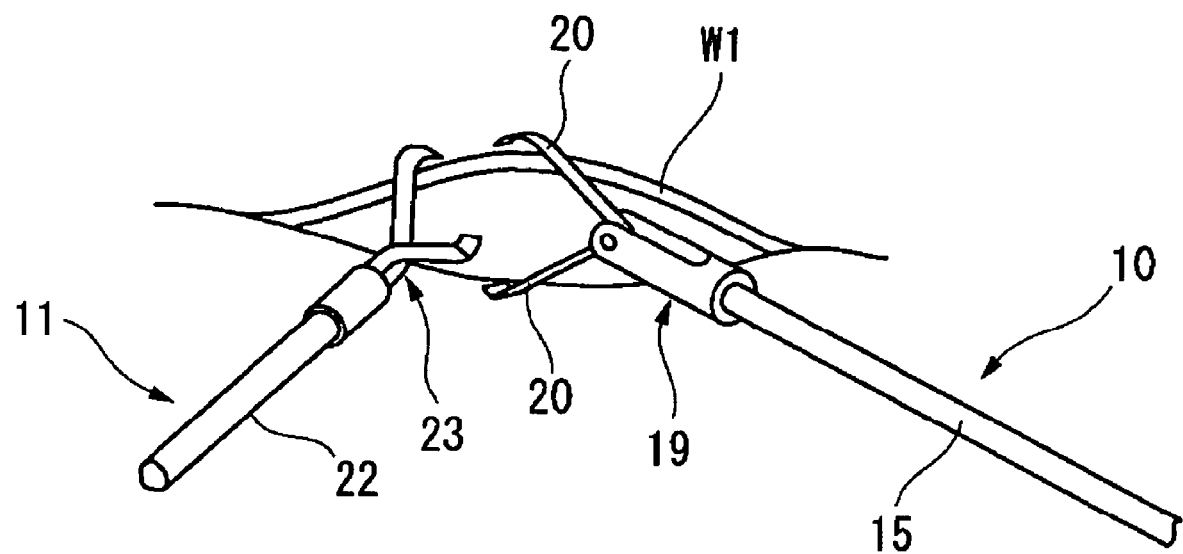
FIG. 4 is a schematic drawing showing a case in which a treatment is carried out for a living organism in an arrangement shown in FIG. 3.

When carrying out the treatment, the operator inserts the pinching forceps 10 and the clip 11 into the body with the insertion part 3, and confirms their position by an illumination means 36 and a CCD 37 provided at the distal portion of the insertion part 3, and then places the distal end treatment unit 19 and the clip unit 23 near the object to be treated. Then, as shown in FIG. 4, the operator pinches a right edge of an incision W1 of the anatomy with the pinching forceps 10 to close the incision W1 and fixes a left edge of the incision W1 with the clip unit 23.

Figure 5:
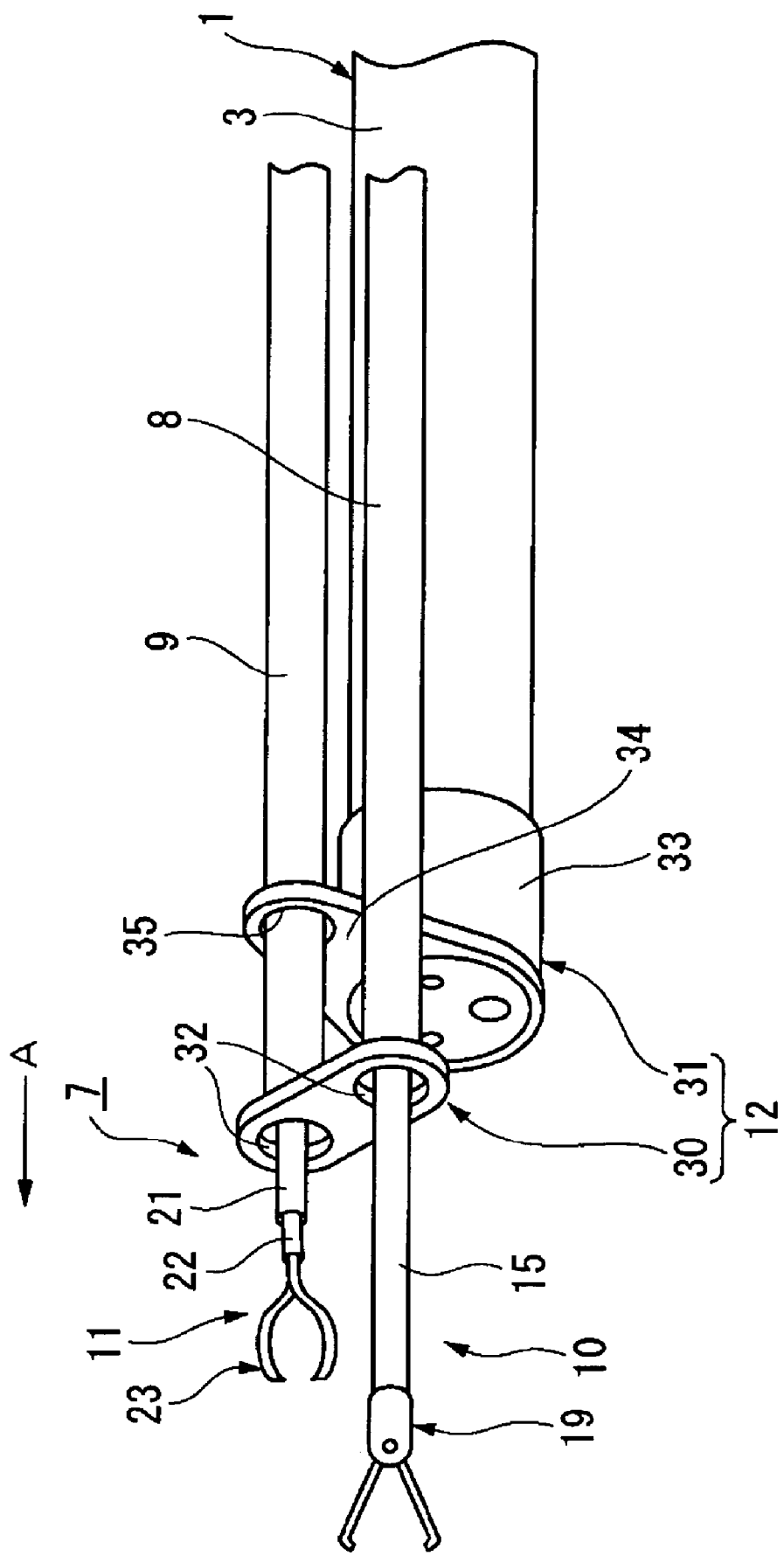
FIG. 5 is a drawing showing a state in which supporting members are rotated and changed from the arrangement shown in FIG. 3 to another arrangement.
Figure 6:
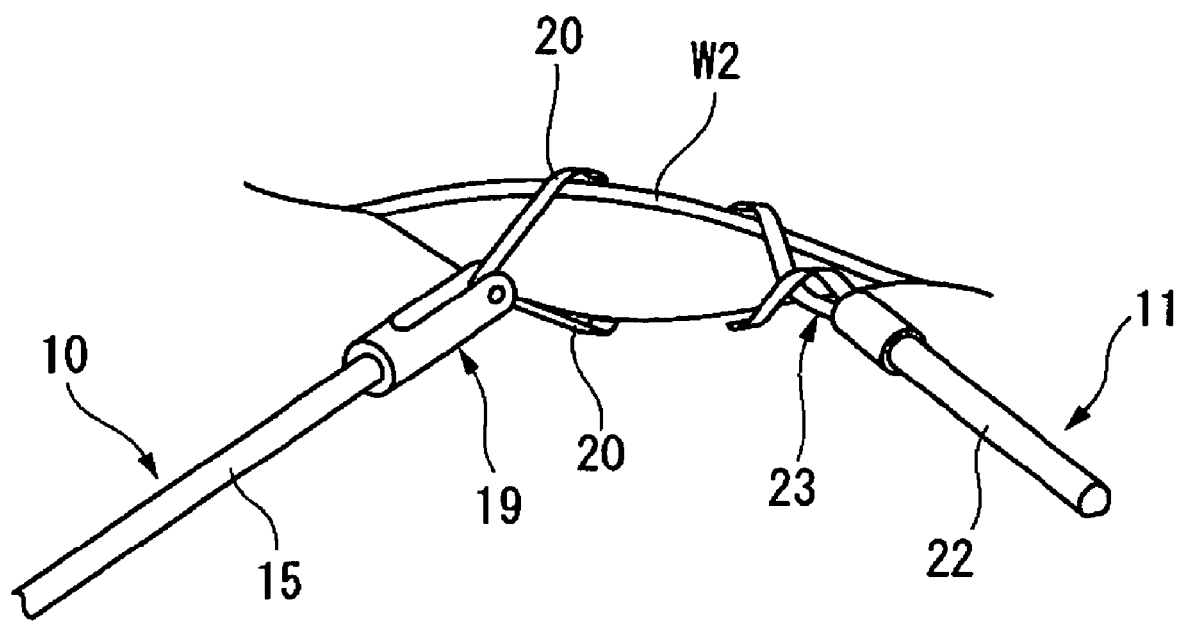
FIG. 6 is a schematic drawing showing a case in which the treatment of the living organisms is carried out in the arrangement shown in FIG. 5.

Here, there are cases in which it is better to pinch the left side of the anatomy to fix the right edge with the clip unit 23 depending on the shape or the position of the incision W1. In this case, the operator takes out the endoscope 1 once, and rotates the supporting member 30 of the supporting adaptor 12 about a longitudinal axis of the second external channel 9. Accordingly, the supporting member 30 rotates about the longitudinal axis extending in parallel with a longitudinal axis of the insertion part 3, and consequently, as shown in FIG. 5, the clip 11 is arranged on the right side when viewed in the direction indicated by Arrow A, so that the pinching forceps 10 is arranged on the left side. When the operator inserts the insertion part 3 again into the body in this state, as shown in FIG. 6, the clip 11 is arranged on the right side and the pinching forceps 10 is arranged on the left side when viewed toward an incision W2 of the anatomy. Therefore, the operator can pinch the left edge of the incision W2 and then fix the right edge therefor with the clip unit 23.

According to the first embodiment, the two external channels 8, 9 are provided, the distal ends of the external channels 8, 9 are fixed by the supporting member 30, and sheaths 15, 21 of the pinching forceps 10 and the clip 11 are slidingly supported by the two external channels 8, 9. Therefore, the pinching forceps 10 and the clip 11 can be mounted to the insertion part 3 with the arrangement fixed. In addition, the supporting member 30 can be rotated with respect to the insertion part 3 by rotatably supporting the second external channel 9 with the sheath supporting section 34 of the fixing cap 31 as the connecting member. Therefore, an orientation of a plane P1 passing through longitudinal axes of the two external channels 8, 9, that is, through the longitudinal axes of two sheaths 15, 21 as shown in FIG. 2 can be changed with respect to a longitudinal axis of the insertion part 3 while the sheaths 15, 21 remain inserted therethrough.

When the supporting member 30 is rotated about the second external channel 9 to exchange the positions of the clip 11 and the pinching forceps 10, the position where the treatment instrument projects is displaced in the field of view of the endoscope. In this case, the displacement can be corrected by rotating the fixing cap 31 with respect to the insertion part 3.

Figure 7:
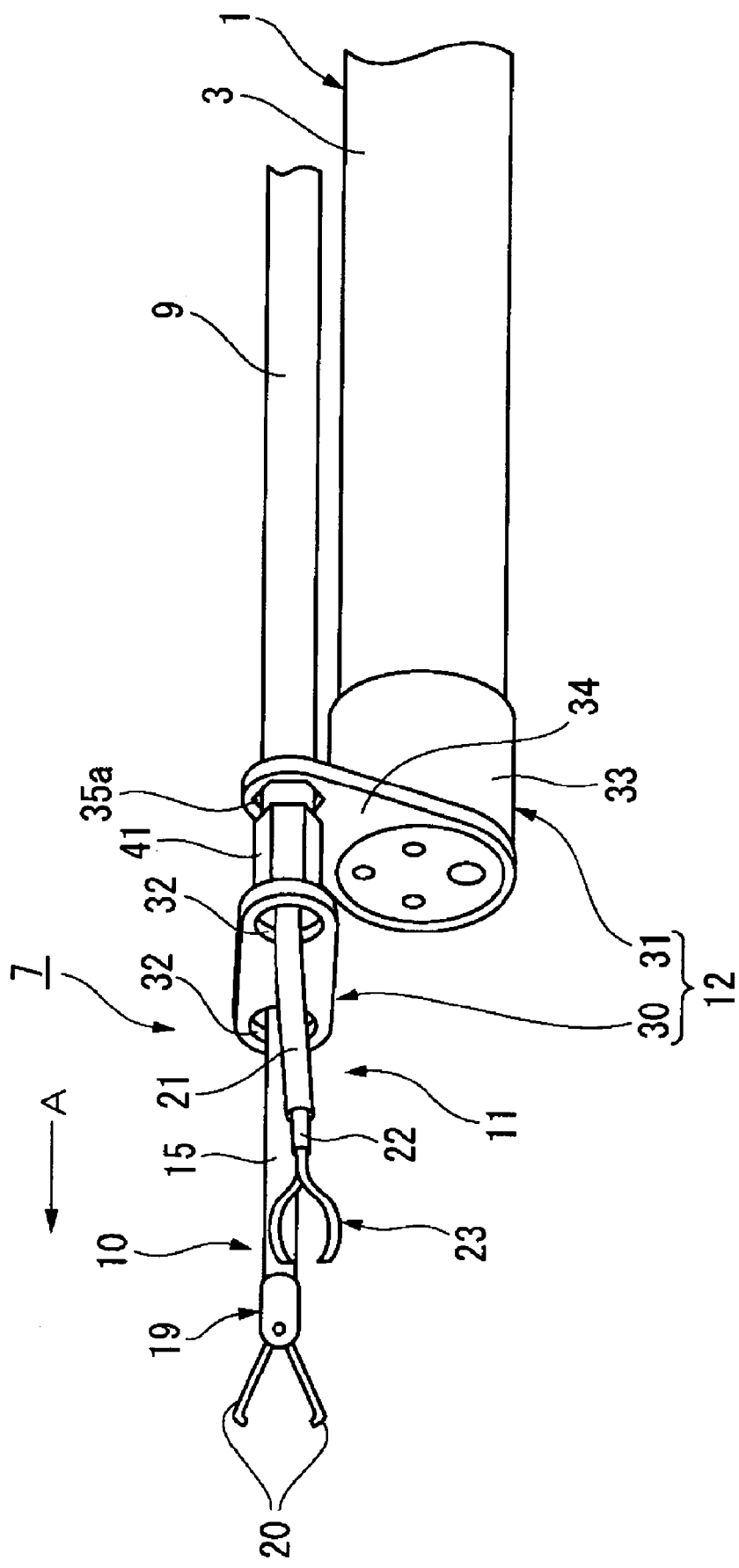
FIG. 7 is a perspective view showing a variation of a distal portion of the treatment instrument of FIG. 3.

As shown in FIG. 7, it is also possible to provide an engaging section 41 being hexagon in contour in the vicinity of the distal portion of the second external channel 9 and to provide a mating hexagonal through hole 35a which can engage thereto on the sheath supporting section 34. In this arrangement, the second external channel 9 and the fixing cap 31 can be engaged with respect to each other only at a rotational angle at which the hexagonal shape on the side of the second external channel 9 and the hexagonal shape on the side of the sheath supporting section 34 coincide with each other. Therefore, the pinching forceps 10 and the clip 11 can be fixed to the insertion part 3 of the endoscope 1 while changing the arrangement thereof at such a specific angle.

Figure 8:
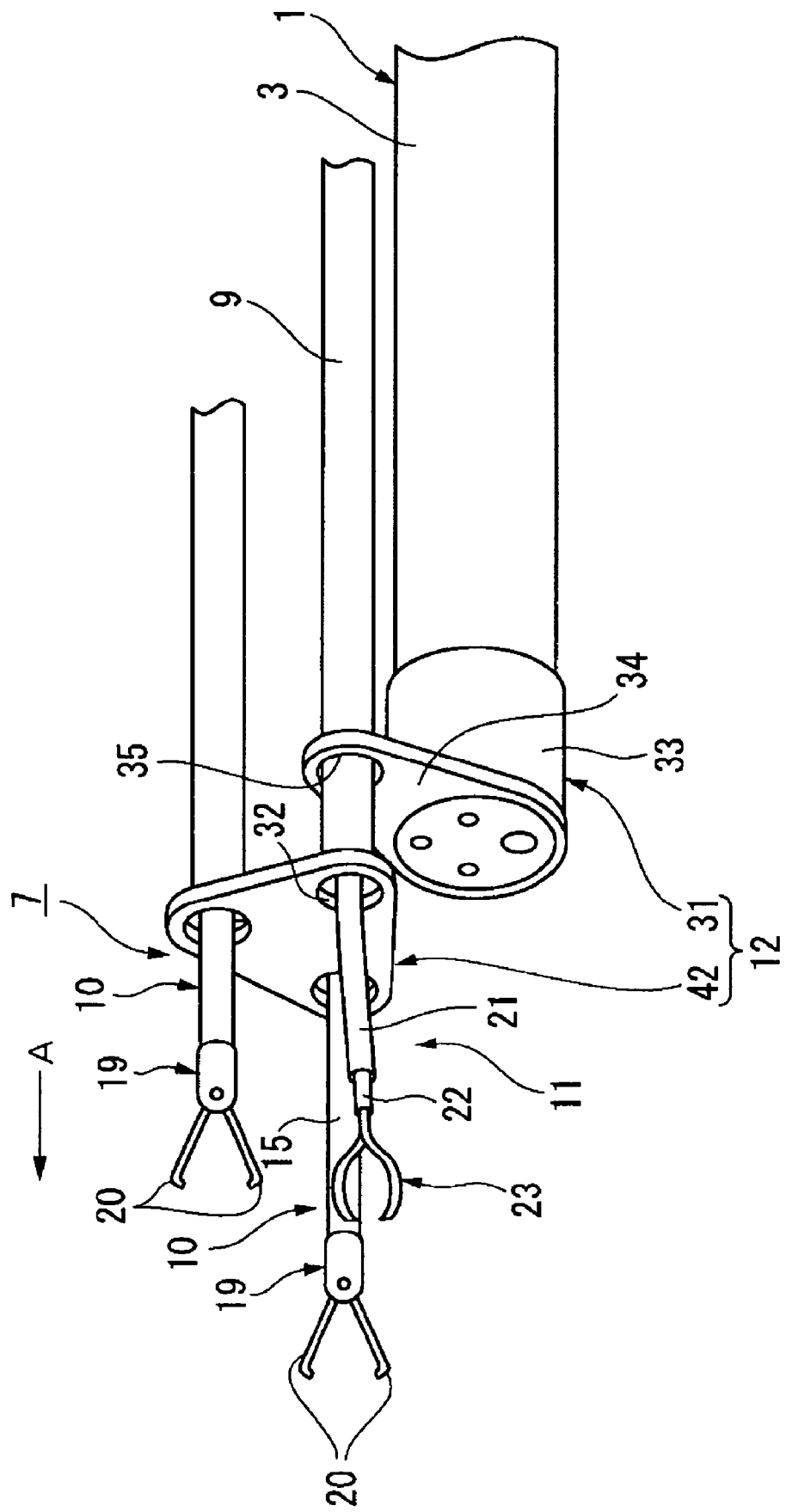
FIG. 8 is a perspective view showing another variation of the distal portion of the treatment instrument of FIG. 3.

As shown in FIG. 8, the supporting adaptor 12 may be provided with a triangular supporting member 42. The triangular supporting member 42 is formed with three through holes 32 at positions corresponding to an apex and three external channels are fixed respectively thereto, so that three sheathes such as the pinching forceps 10 and two of the clips 11 are supported. When changing the arrangement of the pinching forceps 10, the triangular supporting member 42 can be rotated about the longitudinal axis in parallel with the longitudinal axis of the insertion part 3.

Subsequently, referring to the drawings, a second embodiment will now be described. The same parts as in the first embodiment are represented by the same reference numerals and redundant descriptions will be omitted.

Figure 9:
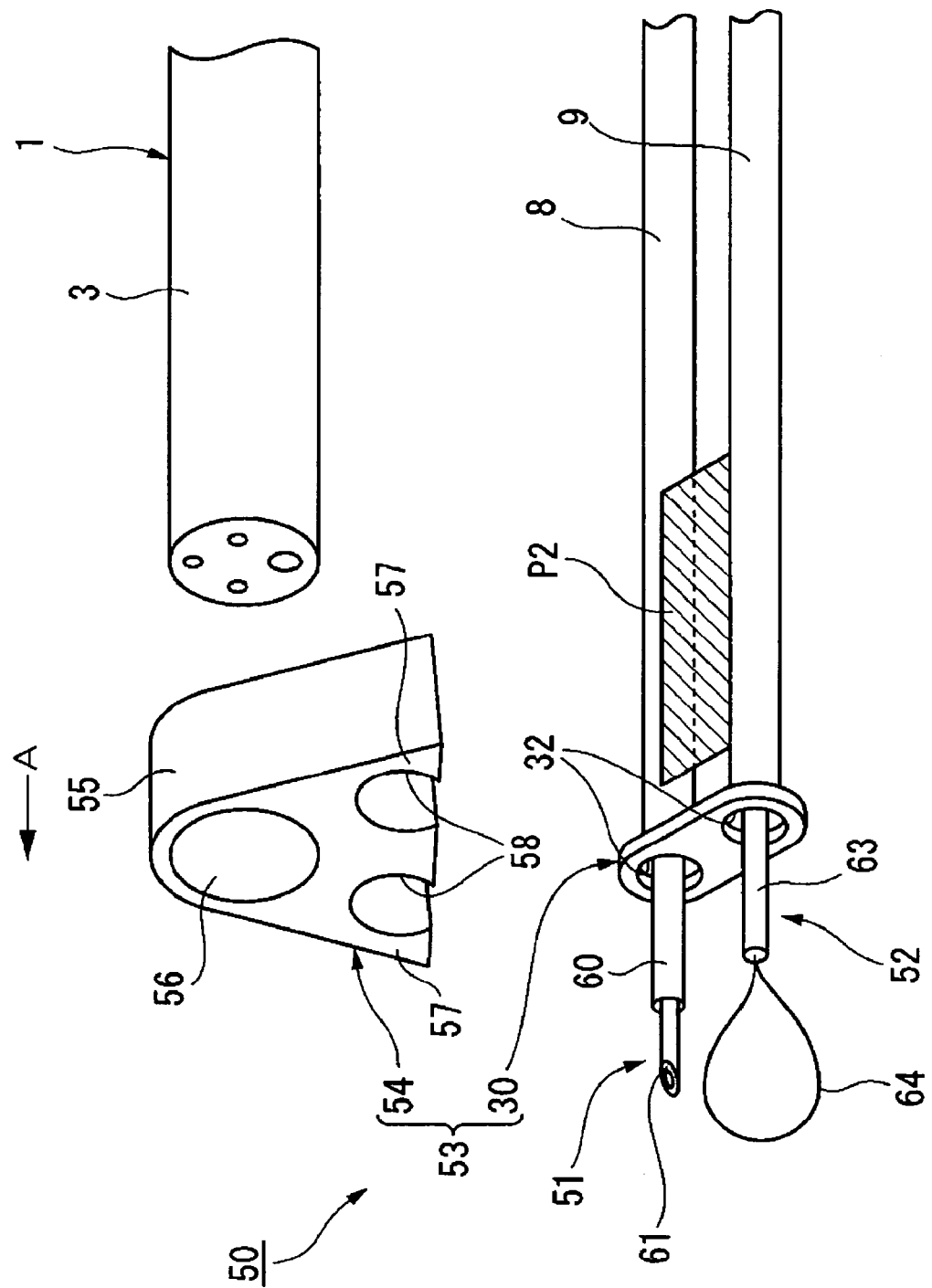
FIG. 9 is a perspective view showing a distal portion of an endoscopic treatment system according to a second embodiment.

As shown in FIG. 9, a treatment instrument 50 includes an injection needle catheter 51, a snare 52, and a supporting adaptor 53, the catheter 51 and snare 52 are inserted respectively into the two external channels 8, 9.

The supporting adaptor 53 includes the supporting member 30 and a connecting member 54, where the connecting member 54 includes an engaging section 55 which is formed with a through hole 56 through which the insertion part 3 can be inserted thereto. Two sheath supporting sections 57 are extended from the engaging section 55. The respective sheath supporting sections 57 are formed with grooves 58 for supporting sheathes 60, 63 for the injection needle catheter 51 and the snare 52 indirectly in parallel with the through hole 56 by detachably fitting one of the first and second external channels 8, 9 therein. In addition, the interval of the grooves 58 of the respective sheath supporting sections 57 is substantially the same as the distance between the through holes 32 of the supporting member 30.

The injection needle catheter 51 includes the flexible sheath 60 which can be inserted into the first external channel 8 so as to be capable of moving back and forth, and the sheath 60 is provided with a needle body 61 as the distal end treatment unit attached to a distal end thereof. The needle body 61 has a cylindrical shape having a distal end that is cut obliquely. The sheath 60 is formed with a lumen in communication with the needle body 61, so that liquid can be supplied from the operating part (for example, the operating part 16 shown in FIG. 1) side.

The snare 52 has the flexible sheath 63 to be inserted into the second external channel 9 so as to be capable of moving back and forth, and the sheath 63 is formed with a lumen therein. An operating wire is inserted into the lumen so as to be capable of moving back and forth, and a snare section 64 with a wire formed into a loop is mounted at a distal end thereof. The snare section 64 is a distal end treatment unit that can be projected from and retracted into the distal portion of the sheath 63 by operating the operating part (for example, the operating part 24 shown in FIG. 1).

In the treatment instrument 50, the operator fits the respective external channels 8, 9 in the grooves 58 to be supported by the supporting member 30 in a state in which the injection needle catheter 51 is inserted through the first external channel 8, and the snare 52 is inserted into the second external channel 9 respectively, so that the external channels 8, 9 are supported by the sheath supporting section 57. Subsequently, the distal portion of the insertion part 3 is inserted into the engaging section 55 of the connecting member 54, and the insertion part 3, the injection needle catheter 51, and the snare 52 are connected via the supporting adapter 53. In this case, the injection needle catheter 51 is arranged on the right side when viewed in a direction indicated by Arrow A, and the snare 52 is arranged on the left side.

When carrying out the treatment, the operator inserts the insertion part 3 into the body, and moves the injection catheter 51 and the snare 52 to a position facing an anatomy to be treated. Then, the operator first punctures the injection needle catheter 51 into the anatomy, injects saline or the like to cause the anatomy to swell. Subsequently, the operator causes the snare section 64 to project from the sheath 63, catches the anatomy in the loop, and then retracts the snare section 64 into the sheath 63 to constrict the anatomy.

Figure 10:
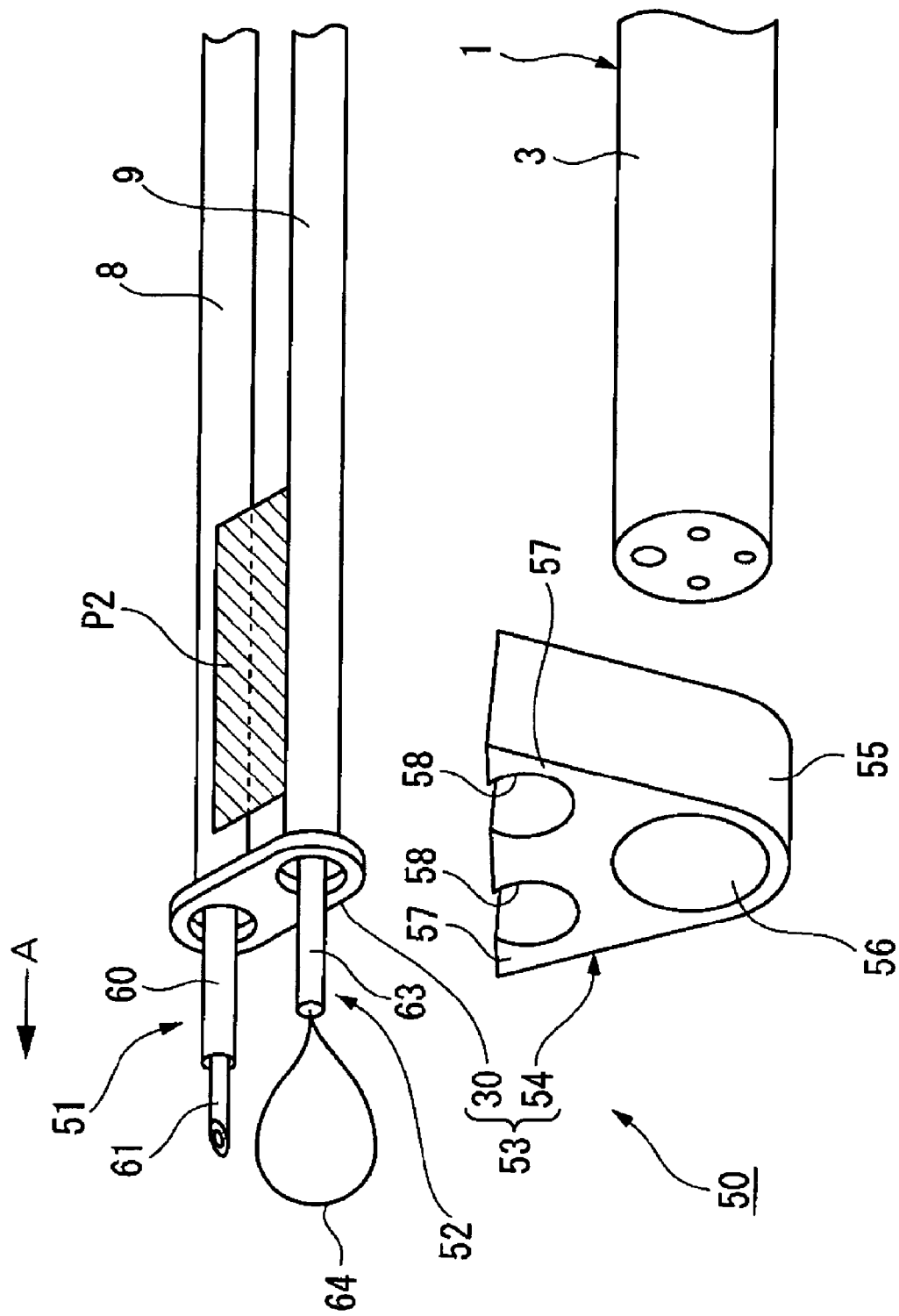
FIG. 10 is a drawing showing a state in which a connecting member is rotated from the state shown in FIG. 7.

In a case in which the puncture from the left side is desired, such as a case in which the injection needle catheter 51 cannot be punctured from the right side when viewed toward the anatomy, the operator removes the insertion part 3 from the body and disconnects the external channels 8, 9 from the sheath supporting section 57. Then, the operator rotates the supporting member 30 about the midsection between the through holes 32 so that the sheathes 60, 63 rotate about a longitudinal axis extending in parallel with a longitudinal axis of the insertion part 3 by 180 degrees, and then engages the first and second external channel 8, 9 with the sheath supporting section 57. Accordingly, as shown in FIG. 10, an orientation of a plane P2 passing through the longitudinal axes of the two external channels 8, 9, that is, the longitudinal axes of the two sheaths 60, 63 is inverted, and the injection needle catheter 51 and the snare 52 are connected to the insertion part 3 in an inverted state with respect to the aforementioned arrangement of FIG. 9. More specifically, the snare 52 is arranged on the right side and the injection needle catheter 51 is disposed on the left side when viewed in the direction of Arrow A. Therefore, when the injection needle catheter 51 is inserted into the body in this state, puncturing of the anatomy from the left side can be achieved.

In the second embodiment, the first and second external channels 8, 9 are detachably supported by the connecting member 54 so that the sheaths 60, 63 can be attached to the insertion part 3 with the relative arrangement fixed. In addition, by rotating the supporting member 30 about its own axis, the injection needle catheter 51 and the snare 52 can be attached to the connecting member 54 with the their positions being exchanged. Accordingly, the arrangement of the injection needle catheter 51 and the snare 52 can be reversed in the lateral direction. Therefore, it is not necessary to remove the sheaths 60, 63 from the external channels 8, 9 every time when exchanging the arrangement of the treatment instrument 50, and hence working efficiency is improved, and manipulation time can be reduced.

Figure 11:
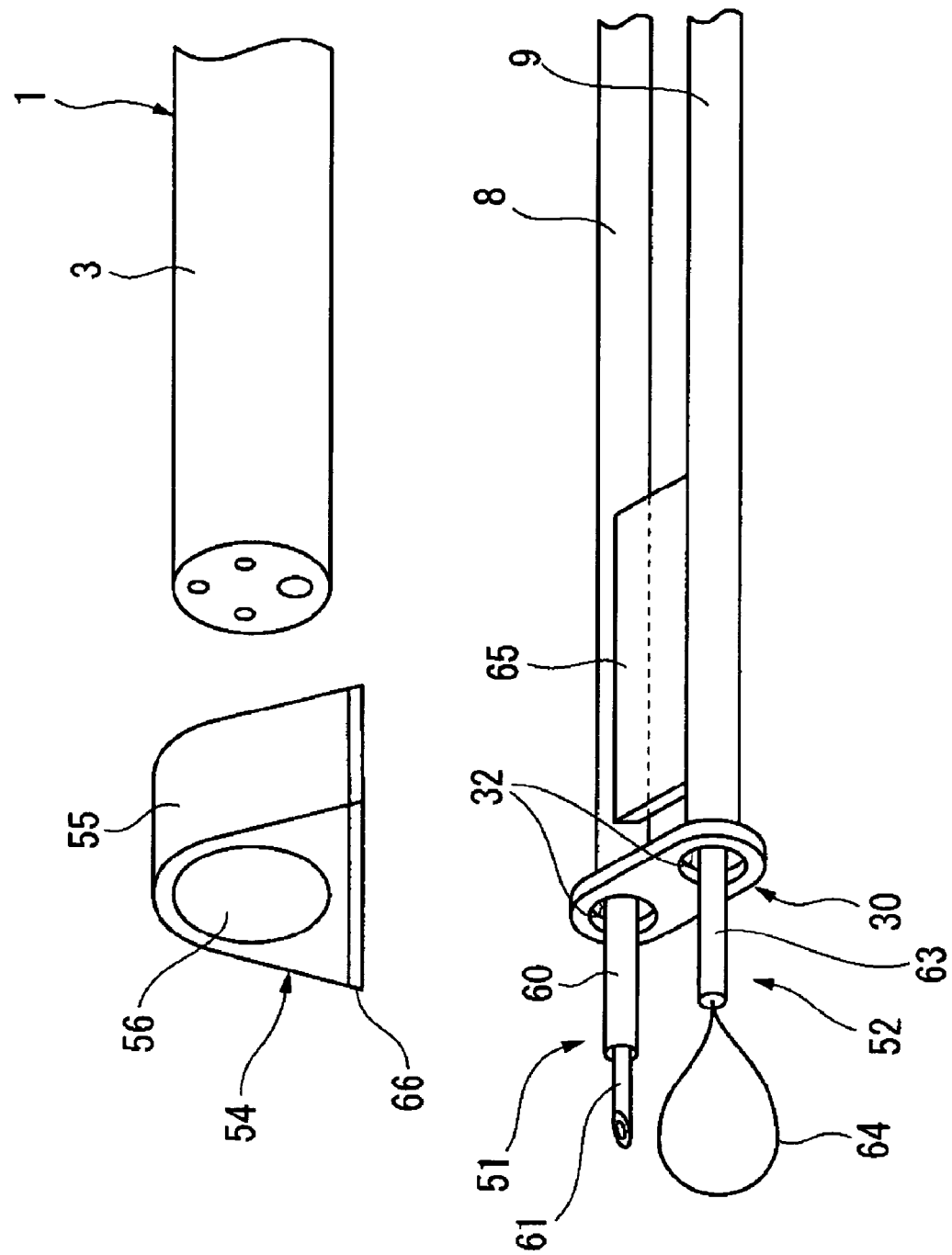
FIG. 11 is a perspective view showing a variation of the distal portion of the treatment instrument of FIG. 9.

It is also possible to provide a plate-shaped magnet 65 connecting the two external channels 8, 9 as shown in FIG. 11. The sheath supporting section of the connecting member 54 comprises a mating magnet 66. The plate magnet 65 is selected such that the both sides of it are attracted by the magnet 66. In this case, attachment and detachment of the external channels 8, 9 can be performed easily by a magnetic force, and the arrangement of the injection needle catheter 51 and the snare 52 can easily be inverted. One of the magnets 65, 66 can be replaced with a metal or resin (magnetic material) which can be attracted to the magnet.

Referring now to the drawings, a third embodiment will be described. The same parts as those in the above-described respective embodiments are represented by the same reference numerals, and redundant description will be omitted.

Figure 12:
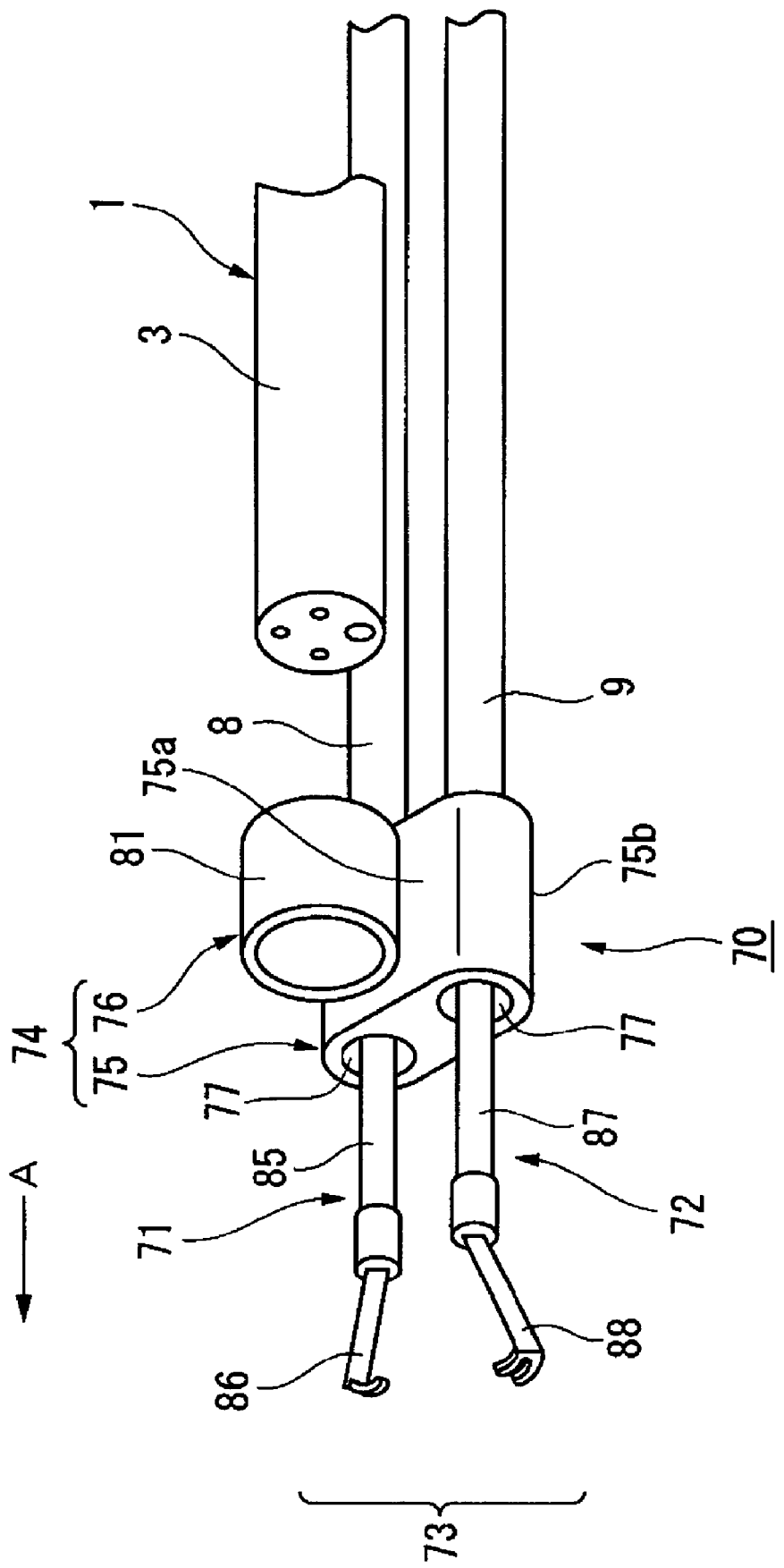
FIG. 12 is a perspective view showing a distal portion of an endoscopic treatment system according to a third embodiment.

As shown in FIG. 12, a treatment instrument 70 includes a pinching forceps 73 provided with a pair of working units 71, 72 inserted into the two external channels 8, 9 respectively, and a supporting adaptor 74. The supporting adaptor 74 includes a supporting member 75 and a connecting member 76 which is detachably attached to the supporting member 75.

The supporting member 75 is formed with two through holes 77 so as to extend in parallel with each other at a predetermined distance, and the external channels 8, 9 are fixed so that the lumens thereof communicate with the through holes 77, respectively. In the supporting member 75, an upper surface 75a and a lower surface 75b which extend substantially in parallel with a plane passing through the longitudinal axes of the through holes 77 are formed with openings 80 of storage grooves 79 as mounting portions (see FIG. 13A). The openings 80 are formed into an elongated shape extending substantially in parallel with the longitudinal axes of the through holes 77, and an inside width of the storage groove 79 is increased in a direction orthogonal to a direction of the length of the opening 80.

As shown in FIG. 13A, the connecting member 76 includes a cylindrical engaging section 81 for inserting the insertion part 3 therein, and the engaging section 81 is provided with a locking fixture 82 extending radially outwardly from the engaging section 81. The locking fixture 82 includes an engaging plate 84 at a distal end of a rod-shaped member 83 fixed to the engaging section 81. The engaging plate 84 being wider than a diameter of the rod-shaped member 83. The engaging plate 84 has a shape which can be inserted into the storage groove 79 through the opening 80 on a side of the supporting member 75.

As shown in FIG. 12, the pinching forceps 73 includes the first working unit 71 to be inserted into the first external channel 8, and the second working unit 72 to be inserted into the second external channel 9. The first working unit 71 includes a working member 86 as the distal end treatment unit rotatably mounted at a distal end of a sheath 85. The second working unit 72 includes a working member 88 as the distal end treatment unit rotatably mounted at a distal end of a sheath 87. Distal ends of the respective working members 86, 88 are bent so as to be engaged with the anatomy easily, and operating wires (not shown) are connected to the respective working members 86, 88. The respective operating wires are inserted into the respective sheaths 85, 87 so as to be capable of moving back and forth, and are mounted to the sliders 18, 26 of the respective operating parts 16, 24, as shown in FIG. 1. Therefore, when the slider 18 is moved back and forth, the operating member 86 rotates, and when the slider 26 is moved back and forth, the working member 88 rotates.

The operation of the third embodiment will now be described.

When the operator mounts the treatment instrument 70 to the endoscope 1, the connecting member 76 is first mounted to the supporting member 75. More specifically, the engaging plate 84 of the connecting member 76 is inserted into the storage groove 79 from the opening 80 of the upper surface 75a of the supporting member 75 in a state in which the connecting member 76 is placed substantially orthogonally to the supporting member 75 as shown in FIG. 13A, then, the connecting member 76 is rotated substantially 90 degrees with respect to the supporting member 75 to bring both of them into a parallel relation, so that the storage groove 79 and the locking fixture 82 are engaged.

Subsequently, the operator inserts the first working unit 71 and the second working unit 72 into the respective external channels 8, 9 one by one. Then, the distal portion of the insertion part 3 of the endoscope 1 is inserted into and engaged with the connecting member 76.

When the treatment is carried out, the operator operates the first working unit 71 and the second working unit 72 independently to pinch the anatomy. In the treatment instrument 70 as described above, for example, by activating one of the working units 71, 72 later than the other, the anatomy can be pinched while drawing the anatomy toward the working units 71, 72. When the insertion part 3 is inserted obliquely into the anatomy, the anatomy can be reliably pinched by activating the working units 86, 88 independently (see FIG. 13B).

Here, when the arrangement of the first and second working units 71, 72 is inverted, the operator removes the supporting member 75 from the connecting member 76, and the supporting member 75 is rotated about a longitudinal axis extending in parallel with the longitudinal axes of the two through holes 77, that is, about longitudinal axes which extends in parallel with the insertion part 3. Subsequently, the lower surface 75b of the supporting member 75 and the connecting member 76 are engaged.

In this embodiment, by engaging and disengaging the locking fixture 82 and the storage groove 79, the first and second external channels 8, 9, and the sheaths 85, 87 are mounted to the insertion part 3 with the arrangement thereof fixed. Therefore, the first and the second working units 71, 72 can be easily attached to and detached from the endoscope 1. In addition, since the supporting member 75 is formed with the storage grooves 79 on the upper surface 75a and the lower surface 75b respectively, the direction of engagement with the locking fixture 82 can be changed by 180 degrees. Therefore, the arrangement of the first and second working units 71, 72 can be changed easily.

Referring now to the drawings, a fourth embodiment will now be described. The same parts as in the above-described respective embodiments are represented by the same reference numerals, and redundant description will be omitted.

Figure 14:
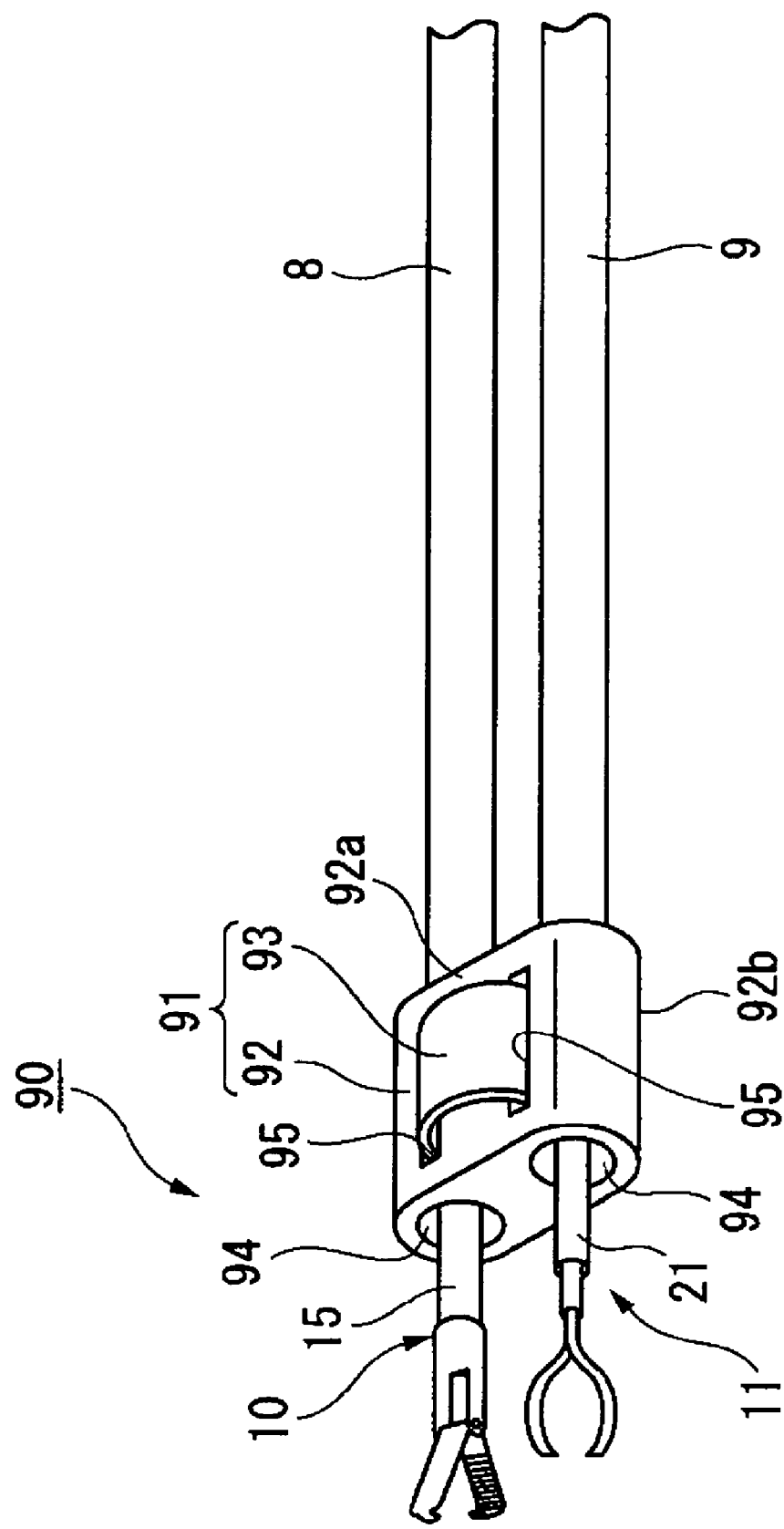
FIG. 14 is a perspective view showing the distal portion of an endoscopic treatment system according to a fourth embodiment.

As shown in FIG. 14, a treatment instrument 90 includes the pinching forceps 10 and the clip 11 to be inserted respectively into the two external channels 8, 9, and a supporting adaptor 91.

The supporting adaptor 91 includes a supporting member 92, and a band 93 as a connecting member inserted into the supporting member 92. The supporting member 92 is formed with two through holes 94 in parallel with each other at a predetermined distance, and the external channels 8, 9 are mounted with the lumens communicated with the respective through holes 94. Formed on the supporting member 92 at a position outside of the through holes 94 in the widthwise direction are slits 95 penetrating from an upper surface 92a to a lower surface 92b of the supporting member 92. The upper surface 92a and the lower surface 92b are outer surfaces extending substantially in parallel with a plane passing through a longitudinal axis of the through holes 94. The slits 95 extend substantially in parallel with the through holes 94 and through which the band 93 is inserted. The band 93 is a member of resilient material, for example, such as rubber formed into an annular shape. A length of the band 93 corresponds substantially to a length through which the inserting portion 3 can be inserted into the band 93 in a state of being inserted into the supporting member 92.

Figure 15:
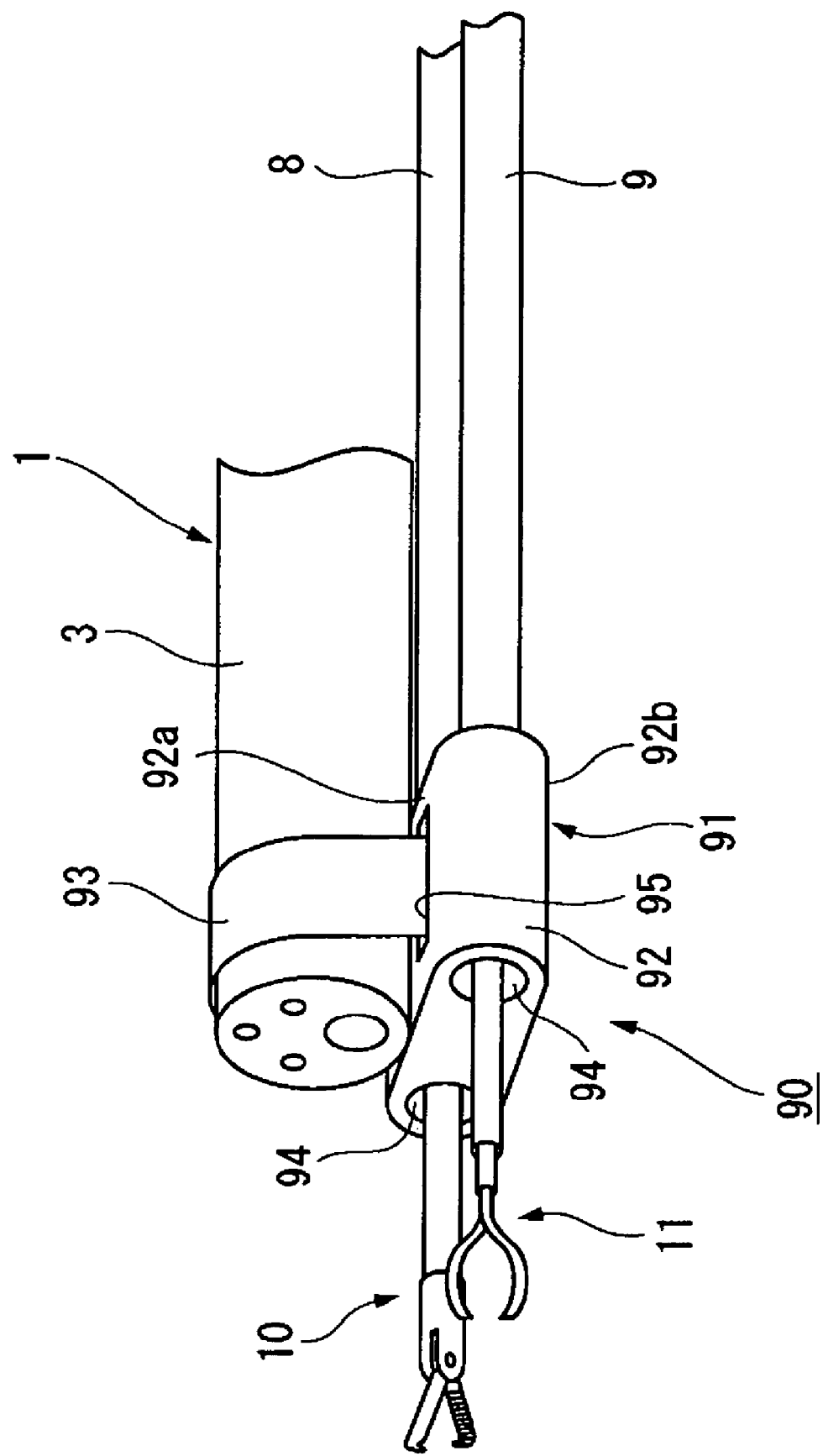
FIG. 15 is a drawing showing a state in which the treatment instrument is attached to the endoscope.

As shown in FIG. 15, when mounting the treatment instrument 90 to the endoscope 1, the operator pulls out the band 93 on the side of the upper surface 92a of the supporting member 92, and inserts the distal portion of the insertion part 3 into the pulled out portion of the band 93. Consequently, the distal portion of the insertion part 3 is engaged with the supporting member 92 with a contracting force and a frictional force of the band 93.

Figure 16:
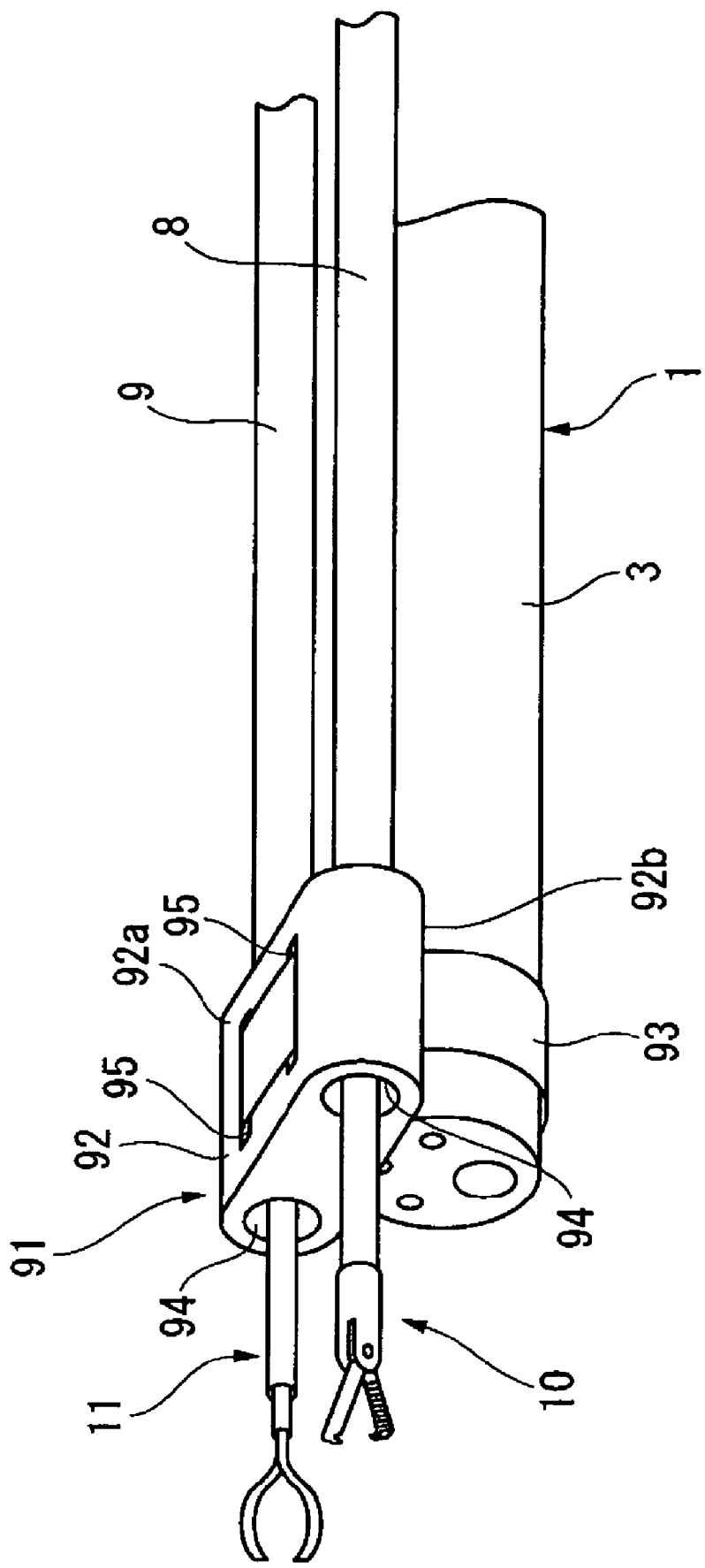
FIG. 16 is a drawing showing a state in which the supporting member is mounted in an inverted position with respect to the position shown in FIG. 13.

When changing the arrangement of the treatment instrument 90, the operator removes the insertion part 3 from the band 93, and rotates the supporting member 92 about a longitudinal axis extending in parallel with the insertion hole 94, that is, about a longitudinal axis extending in parallel with the insertion part 3. Then, the band 93 is pulled out from the lower surface 92b side of the supporting member 92. Then, as shown in FIG. 16, the insertion part 3 is inserted and engaged with the portion of the band 93 pulled away from the lower surface 92b side. Consequently, the treatment instrument 90 is mounted in such a manner that the lower surface 92b of the supporting member 92 faces the insertion part 3, whereby the arrangement of the pinching forceps 10 and the clip 11 is inverted.

In the fourth embodiment, the respective external channels 8, 9, and the respective sheaths 15, 21 can be mounted to the endoscope 1 by engaging the band 93 with the insertion part 3. In addition, the relative position between the pinching forceps 10 and the clip 11 can be fixed by the supporting member 92.

Furthermore, by pulling the band 93, the upper surface 92a or the lower surface 92b of the supporting member 92 can be selectively mounted to the insertion part 3. Therefore, when exchanging the arrangement of the treatment instrument 90, difficulty in withdrawing the sheaths 15, 21 can be eliminated, whereby the manipulation time can be shortened. In addition, since the mounting direction can be switched by only pulling the band 93, the changing operation can be facilitated.

The band 93 can be engaged at a desired position around the insertion part 3. Therefore, even when the pulling direction of the band 93 is not changed, the arrangement of the pinching forceps 10 and the clip 11 can be changed only by engaging the band 93 with the insertion part 3 in a state of being rotated about a longitudinal axis of the insertion part 3 from the position shown in FIG. 15 by 180 degrees.

Subsequently, referring to the drawings, a fifth embodiment will now be described. The same parts as in the above-described respective embodiments are represented by the same reference numerals, and redundant description is omitted.

Figure 17:
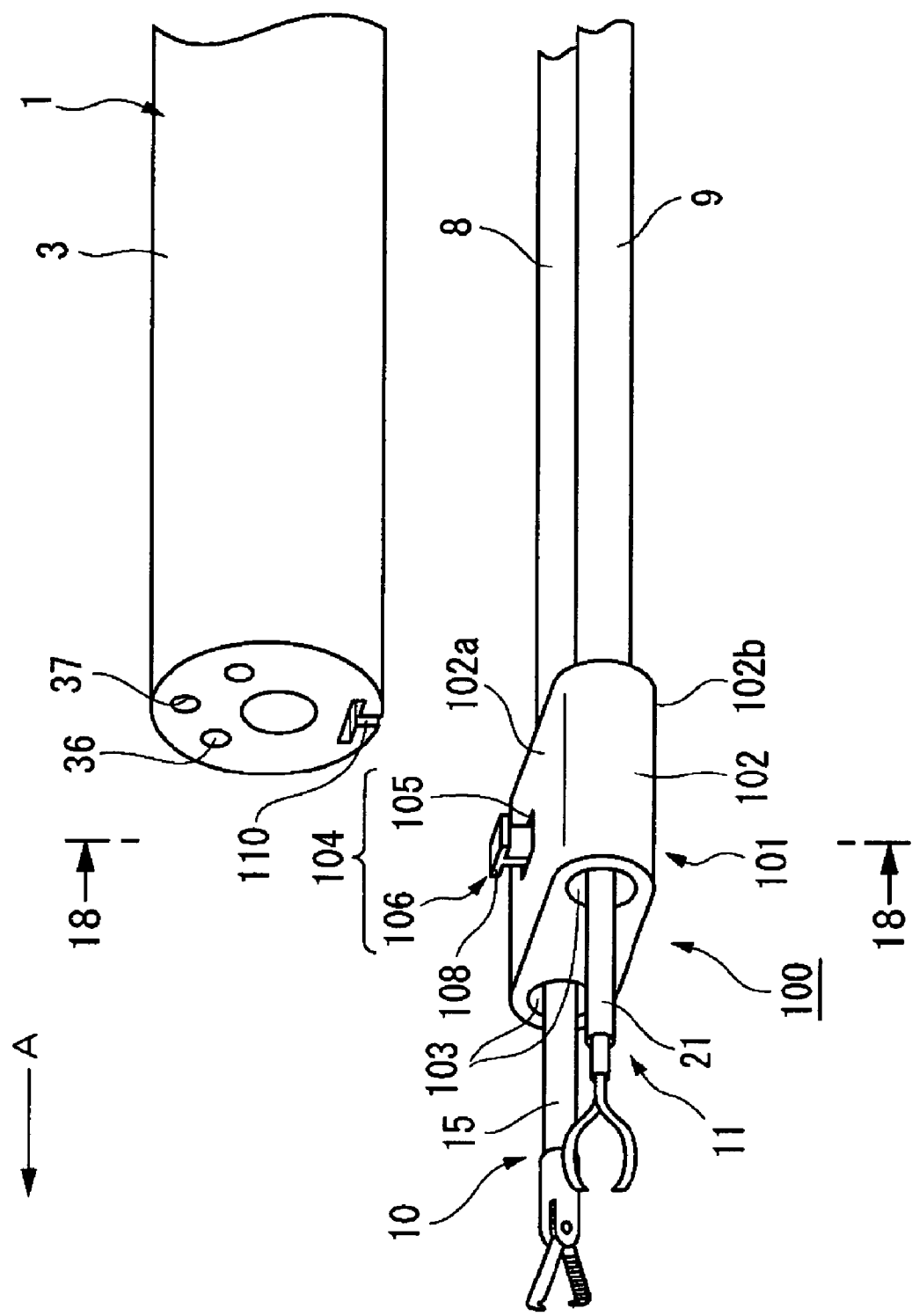
FIG. 17 is a perspective view showing a distal portion of an endoscopic treatment system according to a fifth embodiment.

As shown in FIG. 17, the endoscopic treatment system includes a treatment instrument 100, the endoscope 1, and the first and second external channels 8, 9. The treatment instrument 100 includes the pinching forceps 10 and clip 11 to be inserted into the two external channels 8, 9 respectively, and a supporting adaptor 101.

Figure 18:
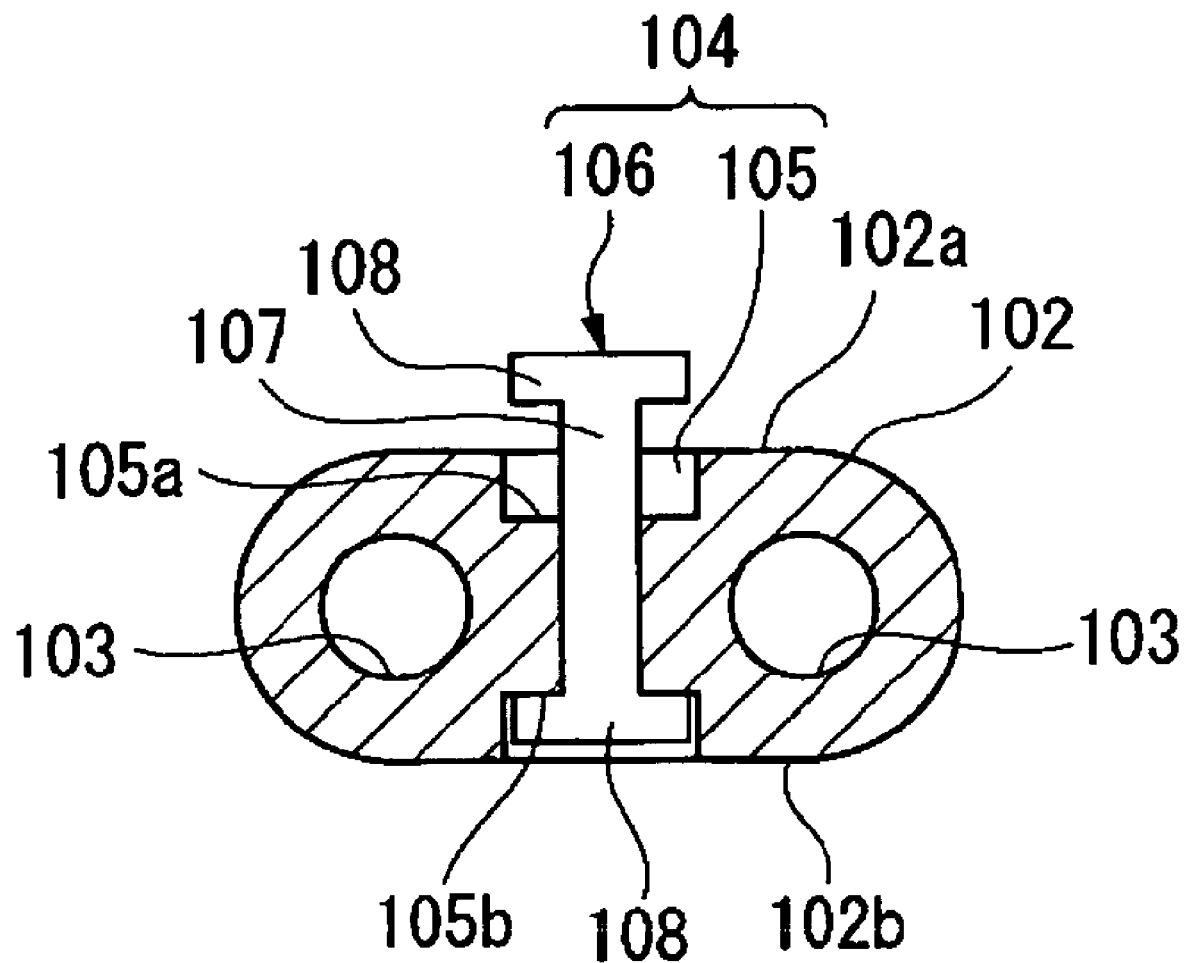
FIG. 18 is a cross-sectional view taken along line 18-18 in FIG. 17.

The supporting adaptor 101 includes a supporting member 102. The supporting member 102 is formed with two through holes 103 so as to extend in parallel with each other at a predetermined distance, and the external channels 8, 9 are mounted so as to communicate the lumens thereof with the respective through holes 103. In addition, provided between the through holes 103 is a mounting mechanism 104. As shown in FIG. 18, the mounting mechanism 104 includes a slide hole 105 penetrating from an upper surface 102a to a lower surface 102b of the supporting member 102, and a lock member 106 as a connecting member which is slidable along the slide hole 105. The slide hole 105 is a shouldered square hole having a wider width at positions near the upper surface 102a and near the lower surface 102b respectively. The lock member 106 is provided with engaging plates 108 having a wider width at both ends of a square rod 107. The distance between the engaging plates 108 is longer than a distance between the upper and lower surfaces 102a, 102b of the supporting member 102, and in a state in which the lower engaging plate 108 comes into abutment with a lower shouldered portion 105b of the slide hole 105, the upper engaging plate 108 projects from the upper surface 102a. Also, in a state in which the upper engaging plate 108 comes into abutment with an upper shouldered portion 105a of the slide hole 105, the lower engaging plate 108 projects from the lower surface 102b.

A single groove 110 is formed on an outer peripheral portion of the distal end of the insertion part 3 of the endoscope 1 along the length of the insertion part 3 from the distal end thereof. The groove 110 is formed into a shape with which the engaging plate 108 and the rod 107 of the lock member 106 can engage, that is, a T-shape when viewed in the direction indicated by Arrow A.

When mounting the treatment instrument 100 to the endoscope 1, for example, the operator engages the lock member 106 with the groove 110 of the insertion part 3 in a state in which the engaging plate 108 is projected from the upper surface 102a of the supporting member 102. Accordingly, the pinching forceps 10 is arranged on the right side and the clip 11 is arranged on the left side in the direction indicated by Arrow A. On the other hand, when changing the arrangement of the pinching forceps 10 or the like, the operator disconnects the supporting member 102 from the insertion part 3, rotates the supporting member 102 about a longitudinal axis thereof extending in parallel with a longitudinal axis of the through hole 103, that is, about a longitudinal axis extending in parallel with the insertion part 3, and then slides the engaging plate 108 of the lock member 106 toward the supporting member 102. Consequently, the engaging plate 108 projects downward from the lower surface 102b, and hence the engaging plate 108 is again brought into engagement with the groove 110 of the endoscope 1. Accordingly, the treatment instrument 100 is engaged with the lower surface 102b of the supporting member 102 facing the insertion part 3, and hence the clip 11 is arranged on the right side and the pinching forceps 10 is arranged on the left side in the direction indicated by Arrow A.

According to the fifth embodiment, the respective external channels 8, 9 and the respective sheaths 15, 21 can be engaged with the insertion part 3 while fixing the relative position thereof by the supporting member 102. In addition, with the provision of the lock member 106 which projects from one of the two opposing surfaces 102a, 102b of the supporting member 102, the supporting member 102 can be mounted to the insertion part 3 in one of two positions, 180 degrees apart. Therefore, the arrangement of the pinching forceps 10 and the clip 11 is quickly changed.

Figure 19:
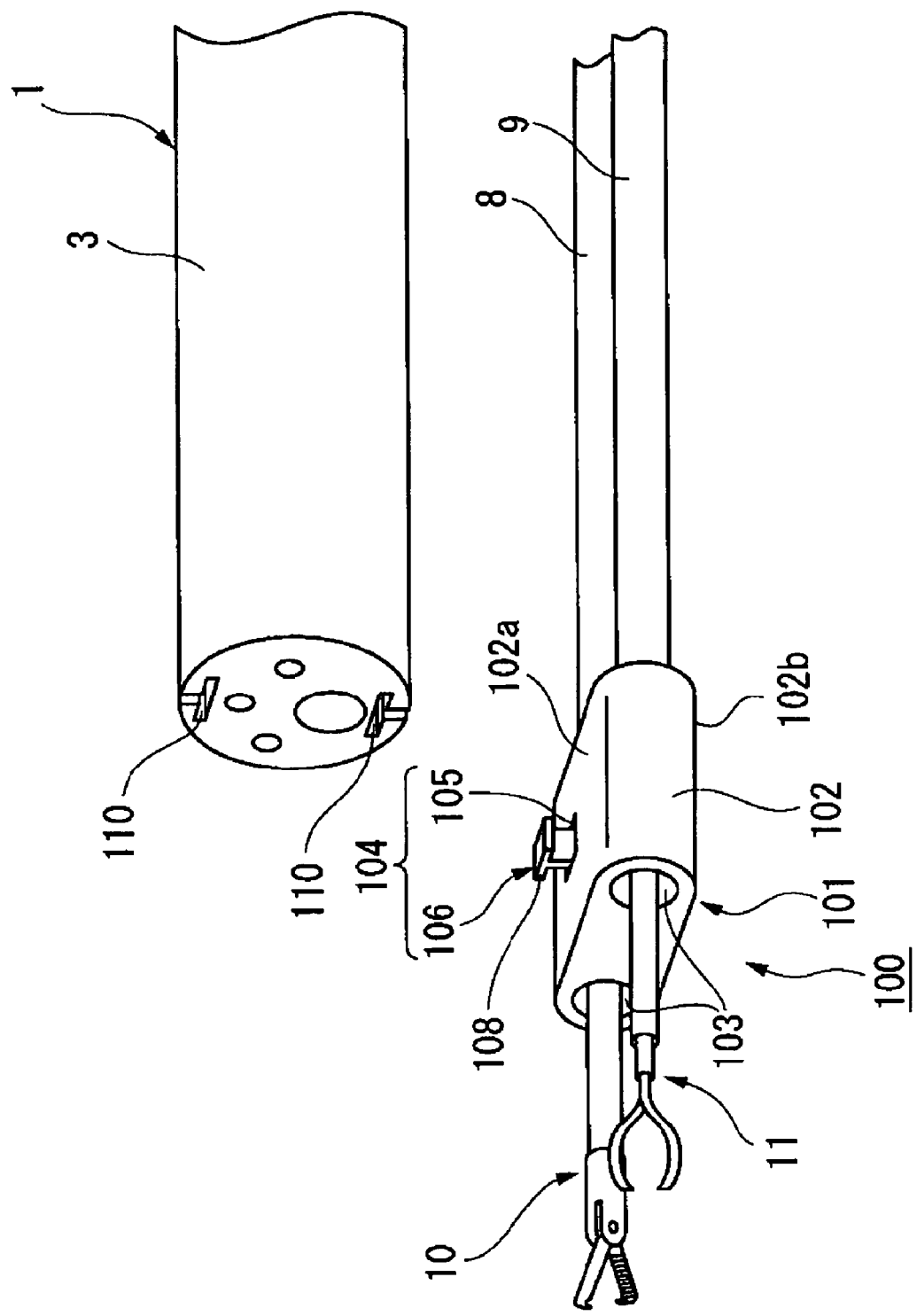
FIG. 19 is a drawing showing a variation of a distal portion of the endoscope insertion part of FIG. 17.

As shown in FIG. 19, two of the grooves 110 may be provided on one diameter of the insertion part 3. In this case, when the mounting position to the insertion part 3 is changed by selecting the groove 110, the projecting position of the treatment instrument 100 can be changed without changing the field of view of the endoscope 1.

Referring now to the drawings, a sixth embodiment will now be described. The same parts as in the above-described respective embodiments are represented by the same reference numerals, and redundant description is omitted.

Figure 20:
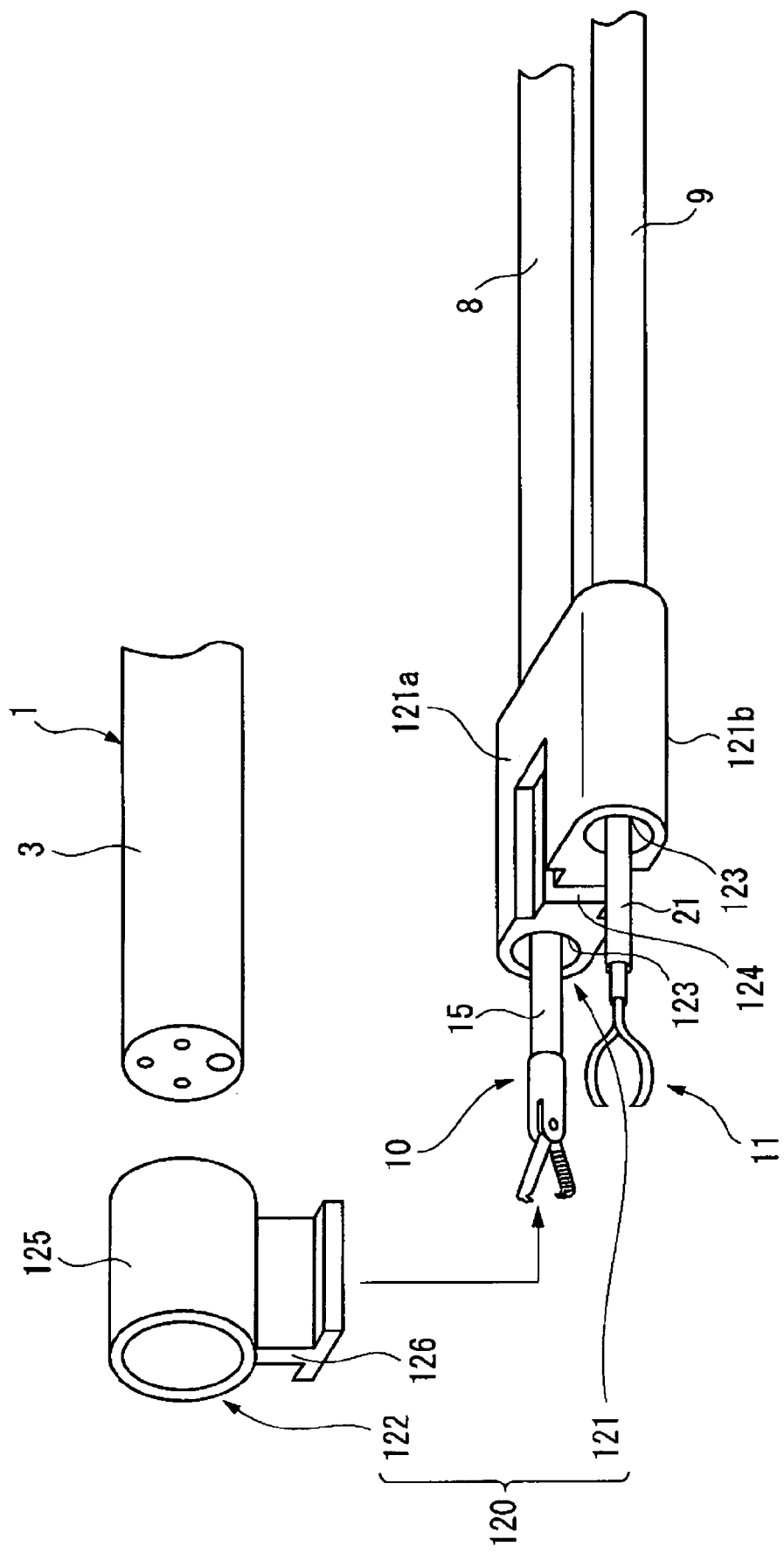
FIG. 20 is an exploded perspective view showing a distal portion of an endoscopic treatment system according to a sixth embodiment.

As shown in FIG. 20, a supporting adaptor 120 includes a supporting member 121 and connecting members 122. The supporting member 121 is formed with two through holes 123 extending in parallel with each other at a predetermined distance, and the external channels 8, 9 are mounted with the lumens thereof communicated with the respective through holes 123. In addition, a rail receiving portion 124, which is a groove penetrated from an upper surface 121a to a lower surface 121b of the supporting member 121, is formed between the through holes 123 so as to extend from a distal end surface of the supporting member 121 in parallel with the through holes 123. The rail receiving portion 124 is notched at an upper surface 121a side and a lower surface 121b side so as to increase in width in a direction orthogonal to the direction of the length of the rail receiving portion 124.

The connecting member 122 includes a cylindrical engaging section 125, which can engage the outside of the insertion part 3, and a rail 126 extending radially outwardly from the engaging section 125. The rail 126 increases in width at a proximal portion and a distal portion of the plate member respectively so as to be formed into an I-shape when viewed in the direction of insertion of the connecting member 122. As described later, the rail 126 is formed into a shape which can be fitted to the rail receiving portion 124 of the supporting member 121.

The operation of the sixth embodiment will now be described.

Figure 21:
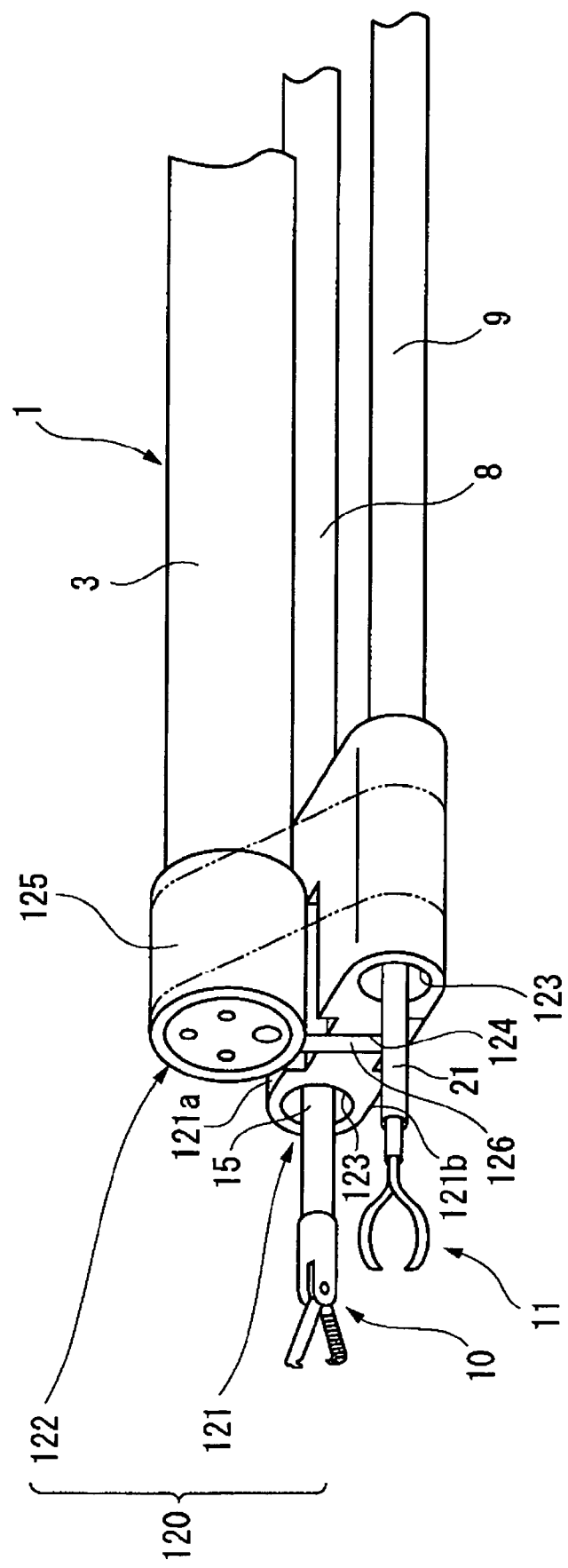
FIG. 21 is a perspective view showing a configuration of the distal portion of the treatment instrument.

The operator inserts, for example, the pinching forceps 10 and the clip 11 in the first and second external channels 8, 9 and through holes 123 of the supporting member 121, respectively. Then, as shown in FIG. 21, the rail 126 of the connecting member 122 mounted to the insertion part 3 is inserted and fitted into the rail receiving portion 124 of the supporting member 121. When the connecting member 122 is arranged to the upper surface 121a side of the supporting member 121, the distal end of the rail engages the widened portion of the rail receiving portion 124 on the lower surface 121b side, and the arrangement of the pinching forceps 10 and the clip 11 is fixed to the endoscope 1. When firm fixation of the supporting member 121 is desired, the supporting member 121 can also be fixed to the insertion part 3 by tape (shown in broken lines) or the like.

When a change of the arrangement of the pinching forceps 10 and the clip 11 in the lateral direction is desired, the operator removes the rail 126 from the rail receiving portion 124, inverts the supporting member 121 so that the lower surface 121b faces the connecting member 122, and then inserts the rail 126 into the rail receiving portion 124. The distal end of the rail 126 engages the widened portion of the rail receiving portion 124 on an upper surface 124a side, and is mounted to the insertion part 3 with the arrangement of the pinching forceps 10 and the clip 11 inverted in the lateral direction. When changing the arrangement, the connecting member 122 can be rotated around the insertion part 3 without changing the arrangement of the connecting member 122 and the supporting member 121, or may be mounted at different rotational angles.

According to the sixth embodiment, the supporting member 121 can be mounted to the insertion part 3 easily by sliding the supporting member 121 relative to the connecting member 122. In this case, since the rail receiving portion 124 is formed so as to receive the rail 126 from both of the upper surface 121a side and the lower surface 121b side, the arrangement of the pinching forceps 10 and the clip 11 can be changed easily by inverting the direction of fitting with respect to the rail 126.

Referring now to the drawings, a seventh embodiment will now be described. The same parts as in the above-described respective embodiment are represented by the same reference numerals, and redundant description is omitted.

Figure 22:
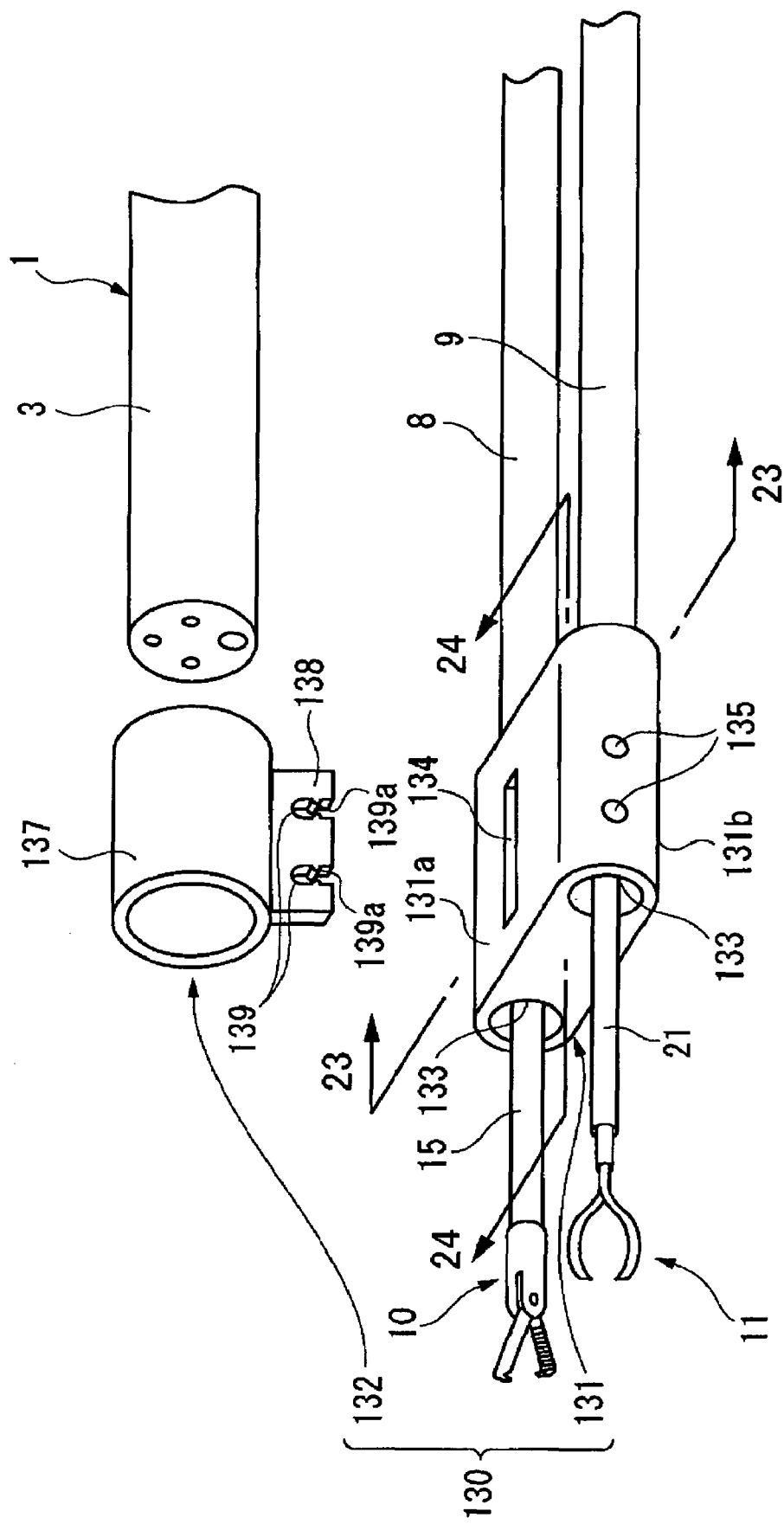
FIG. 22 is an exploded perspective view showing a distal portion of an endoscopic treatment system according to a seventh embodiment.
Figure 23:
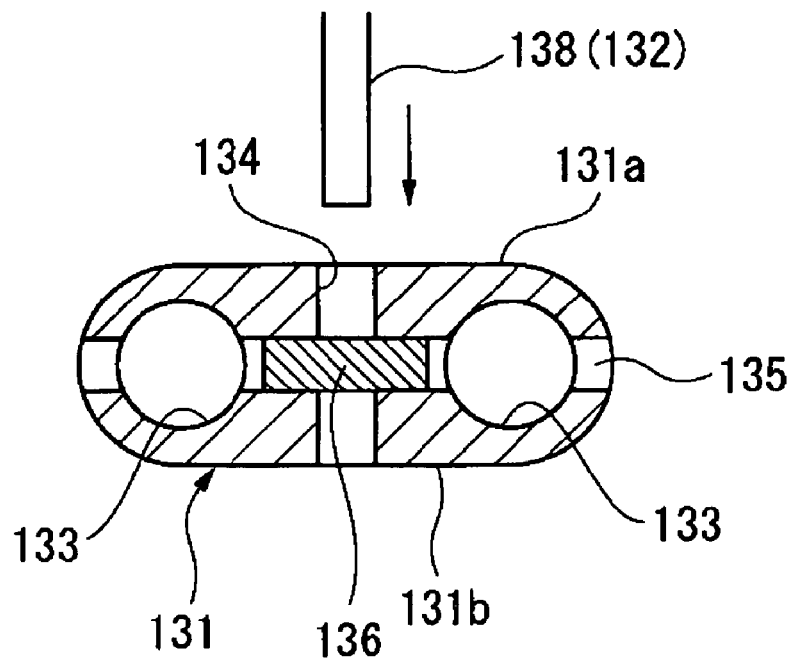
FIG. 23 is a cross-sectional view taken along line 23-23 in FIG. 22.

As shown in FIG. 22 and FIG. 23, a supporting adaptor 130 includes a supporting member 131 and a connecting member 132. The supporting member 131 is formed with two through holes 133 extending in parallel with each other at a predetermined distance, and is mounted, and the external channels 8, 9 are mounted with the lumens thereof communicated with the respective through holes 133. Formed between the through holes 133 is an elongated hole 134 penetrating from an upper surface 131a to a lower surface 131b of the supporting member 131 so as to extend in parallel with the through holes 133. In addition, as shown in FIG. 23, side holes 135 penetrating through the supporting member 131 are formed so as to be orthogonal to the through holes 133 and the elongated hole 134 respectively, and pins 136 are slidably inserted into the side holes 135. As shown in FIG. 22, two of the side holes 135 are formed in parallel with each other along the direction of the length of the through hole 133.

Figure 24:
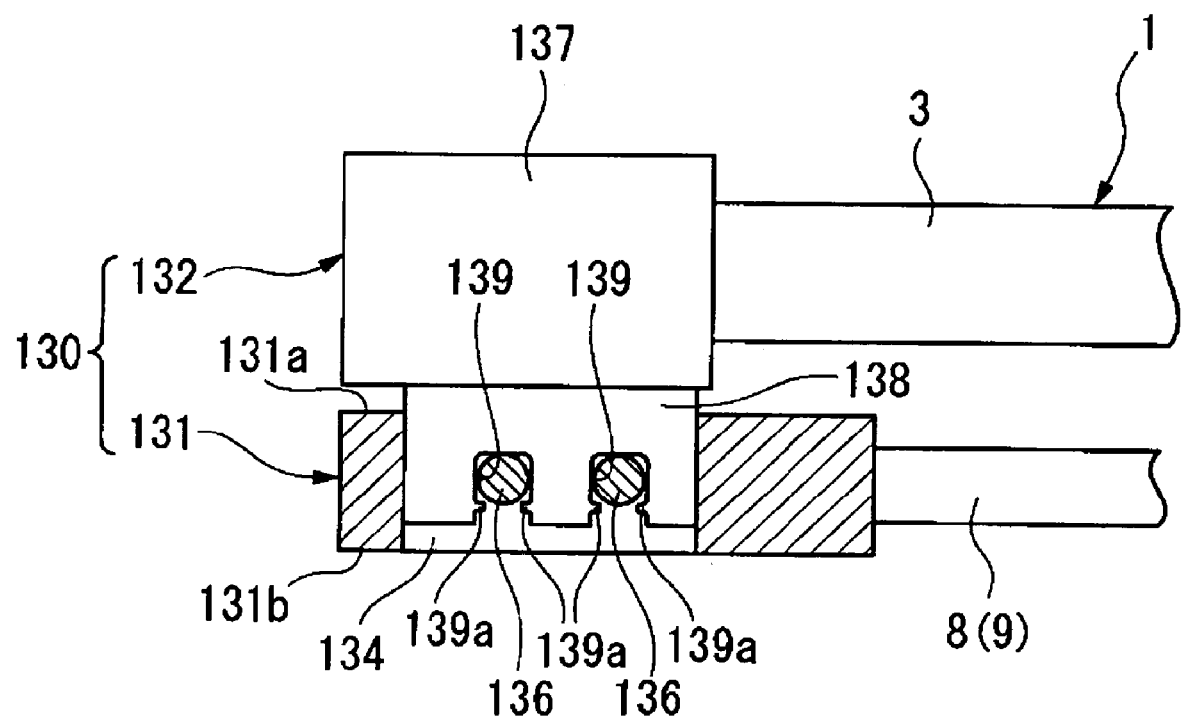
FIG. 24 is a cross-sectional view taken along line 24-24 in FIG. 22.

The connecting member 132 includes a cylindrical engaging section 137 that can engage the outside of the insertion part 3, and an insertion strip 138 extends from the engaging section 137 radially outwardly. The insertion strip 138 is formed with two notches 139 on the distal end side along the length thereof. Each notch 139 extends from the distal end of the insertion strip 138 in the direction of the length of the engaging section 137 and is formed with projections 139a at the midsections thereof so as to reduce a width thereof. As shown in FIG. 24, the insertion strip 138 is formed into a shape that can be inserted into the elongated hole 134 of the supporting member 131. The pin 136 fixed at both ends to the supporting member 131 extends through the elongated hole 134 in the lateral direction. An area from the projections 139a to a terminal of the notch 139 is formed in which the pin 136 can be fitted when the insertion strip 138 is inserted into the elongated hole 134. The length of the notch between the opposed projections 139a is shorter than the contour of the pin 136.

The operation of the seventh embodiment will now be described.

The operator first inserts the insertion strip 138 of the connecting member 132 into the elongated hole 134 of the supporting member 131. When it is inserted until it abuts against the upper surface 131a of the supporting member 131, the projections 139a plastically deform over the pins 136 so that the pins 136 are accommodated in the terminal sides of the notches 139, whereby the supporting members 131 and the connecting members 132 are engaged with respect to each other. In addition, for example, the pinching forceps 10 and the clip 11 are inserted respectively into the first and second external channels 8, 9 and the through holes 133 of the supporting member 131, respectively.

When inverting the arrangement of the pinching forceps 10 and the clip 11 in the lateral direction, the operator retracts the pinching forceps 10 and the clip 11 from the supporting member 131 once, and then the insertion strip 138 is pulled out from the insertion hole 134. Then, the insertion strip 138 is inserted from the opposite side, that is, so that the engaging section 137 abuts against the lower surface 131b of the supporting member 131. Thereafter, when the pinching forceps 10 and the clip 11 are inserted again into the supporting member 131, the arrangement can be inverted. When changing the arrangement, the connecting member 132 can be rotated about the insertion part 3 without changing the arrangement of the connecting member 132 and the supporting member 131, or may be mounted at a different rotational angle.

According to the seventh embodiment, the connecting member 132 can be mounted easily to the insertion part 3. In this case, the insertion strip 138 is formed so that the notches 139 and the side holes 135 coincide with each other even when it is inserted from the lower surface 131b side, the arrangement of the pinching forceps 10 and the clip 11 can be changed easily by inverting the direction of insertion of the insertion strip 138.

The endoscopic systems and components thereof disclosed above have wide applications and are not limited to the above-described respective embodiments.

For example, in the respective embodiments, combinations of the pinching forceps 10 and the clip 11, or the injection needle catheter 51 and the snare 62, or the first working unit 71 and the second working unit 72 can be selected as needed, and a combination with other treatment units is also applicable. As a detailed example of a combination which demonstrates enhanced performance, the combinations of the pinching forceps 10 and the clip 11, the pinching forceps 10 and the snare 62, the pinching forceps 10 and a scissors forceps, the pinching forceps 10 and a hot biopsy forceps, the pinching forceps 10 and a heat probe, and the pinching forceps 10 and an indwelling snare can also be used.

Figure 25:
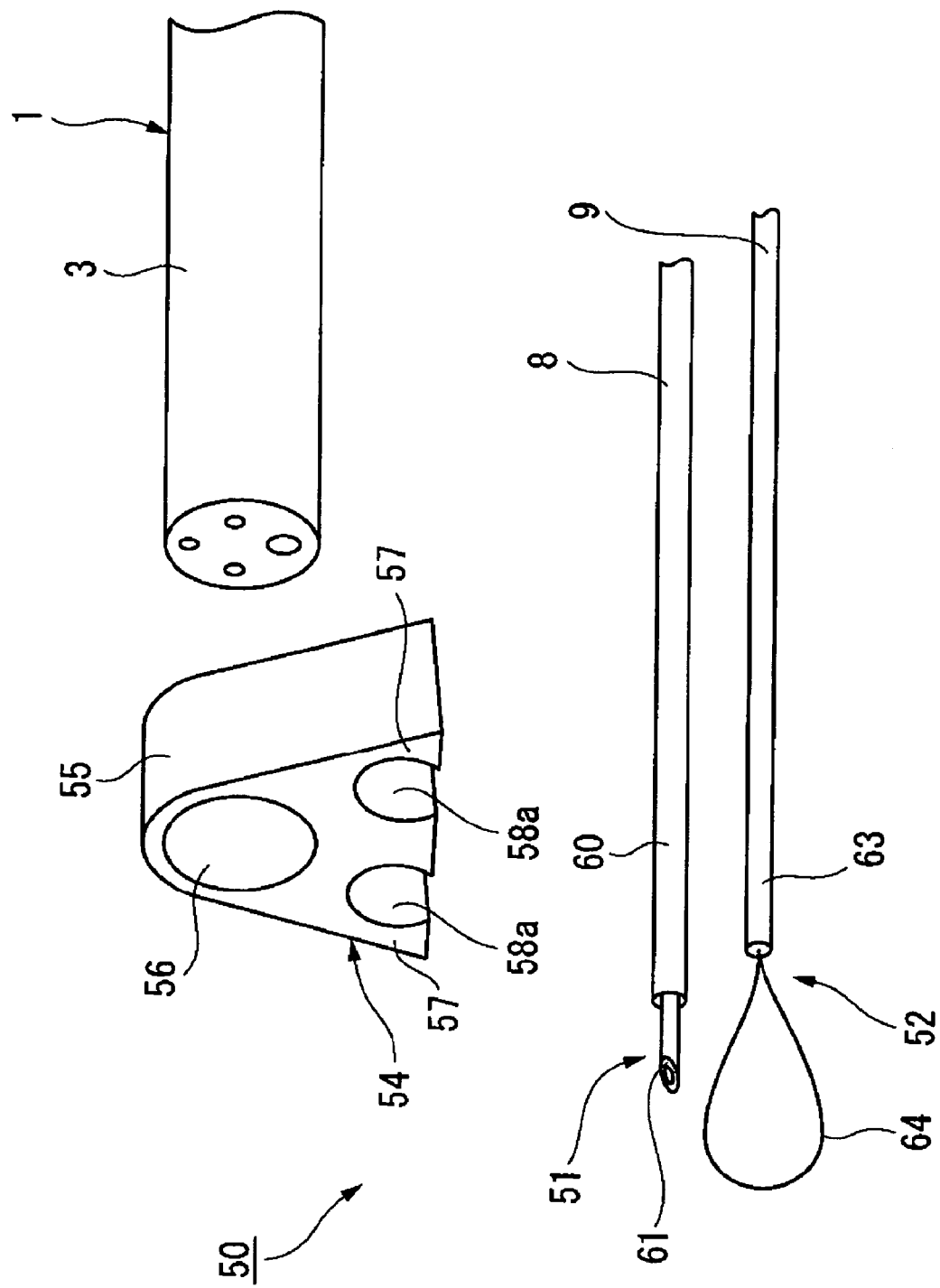
FIG. 25 is an exploded perspective view showing a configuration of the distal portion of the treatment instrument.

The respective supporting members 30, 75, 92, 102 may be configured in such a manner that the first and second external channels 8, 9 are detachably attached. As shown in FIG. 25, the respective supporting members 30, 75, 92, 102 may be configured so as to support the sheaths 60, 63 directly without the intermediary of the external channels. In this case, two grooves 58a to which the sheaths 60, 63 are detachably attached are provided so as to extend in parallel with each other on the sheath supporting portion 57 of the connecting member 54.

In addition, the connecting members 31, 54, 76 may be fixed to the insertion part 3 in advance. In this case, they may be mounted so as to be rotatably about a longitudinal axis of the insertion part 3.

While there has been shown and described what are considered to be preferred embodiments of the invention, it will, of course, be understood that various modifications and changes in form or detail could readily be made without departing from the spirit of the invention. It is therefore intended that the invention not be limited to the exact forms described and illustrated, but constructed to cover all modifications that may fall within the scope of the appended claims.

What is claimed is:

1. An endoscopic treatment instrument to be inserted into a body together with an endoscope insertion part for carrying out a treatment for living organisms, the endoscopic treatment instrument comprising:

a plurality of elongated flexible sheaths;

an operating part provided at a proximal portion of each of the plurality of flexible elongated sheaths;

a distal end treatment unit provided at a distal portion of each of the plurality of flexible elongated sheaths for carrying out a treatment for living organisms;

a supporting member for directly or indirectly supporting the plurality of flexible elongated sheaths disposed substantially in parallel with the endoscope insertion part for constraining a relative position of the plurality of flexible elongated sheaths; and a connecting member for directly or indirectly connecting the sheaths and the endoscope insertion part;

wherein the position of the supporting member relative to the connecting member is changeable at least in a direction perpendicular to the endoscopic insertion part to change the arrangement of the plurality of sheaths with respect to the endoscope insertion part.

2. The endoscopic treatment instrument according to claim 1, wherein the supporting member is brought into a state of at least being rotated about a longitudinal axis extending substantially in parallel with a longitudinal axis of the endoscope insertion part by changing the connecting state of the connecting member.

3. The endoscopic treatment instrument according to claim 2, wherein the state of at least being rotated is a state in which the supporting member is inverted about the longitudinal axis extending substantially in parallel with the longitudinal axis of the endoscope insertion part.

4. The endoscopic treatment instrument according to claim 1, wherein the connecting member comprises a rotary supporting section for supporting one of the plurality of elongated flexible sheaths so as to be capable of rotating about a longitudinal axis of one of the plurality of elongated flexible sheaths.

5. The endoscopic treatment instrument according to claim 4, wherein the connecting member comprises an engaging section which engages the endoscope insertion part so as to be capable of rotating therearound.

6. The endoscopic treatment instrument according to claim 5, wherein the engaging section is configured to be detachable with respect to the endoscope insertion part.

7. The endoscopic treatment instrument according to claim 1, wherein the connecting member is formed with a plurality of sheath supporting sections for supporting the plurality of elongated flexible sheaths so as to be capable of replacement.

8. The endoscopic treatment instrument according to claim 1, wherein the supporting member comprises mounting parts used for fixing the supporting member to the endoscope insertion part by the same number as possible arrangements as the arrangement of the plurality of elongated flexible sheaths.

9. The endoscopic treatment instrument according to claim 1, wherein the connecting member is provided so as to be capable of moving in a direction substantially orthogonal to a plane defined by the plurality of elongated flexible sheaths.

10. An endoscopic treatment system comprising:
an endoscope having an endoscope insertion part for carrying out a treatment for living organisms; and
an endoscopic treatment instrument comprising:
- a plurality of elongated flexible sheaths;
- an operating part provided at a proximal portion of each of the plurality of flexible elongated sheaths;
- a distal end treatment unit provided at a distal portion of each of the plurality of flexible elongated sheaths for carrying out a treatment for living organisms;
- a supporting member for directly or indirectly supporting the plurality of flexible elongated sheaths disposed substantially in parallel with the endoscope insertion part for constraining a relative position of the plurality of flexible elongated sheaths; and
- a connecting member for directly or indirectly connecting the sheaths and the endoscope insertion part;
- wherein the position of the supporting member relative to the connecting member is changeable at least in a direction perpendicular to the endoscopic insertion part to change the arrangement of the plurality of sheaths with respect to the endoscope insertion part;
wherein the endoscope insertion part comprises a fixing device for engaging the connecting member.

11. The endoscopic treatment system according to claim 10,
wherein the fixing device comprises a groove provided along a direction of a length of the endoscope insertion part and a corresponding mating projection on the connecting member.

* * * * *